(12) United States Patent
Jung et al.

(10) Patent No.: US 9,056,302 B2
(45) Date of Patent: Jun. 16, 2015

(54) HIGHLY BRANCHED POLYMERS AS CROSS-LINKING AGENTS IN MICROCAPSULE WALL

(75) Inventors: Marc Rudolf Jung, Worms (DE); Francisco Javier Lopez Villanueva, Mannheim (ES); Tina Schroeder-Grimonpont, Rheinzabern (DE); Monika Haberecht, Ludwigshafen (DE); Bernd Bruchmann, Freinsheim (DE)

(73) Assignee: BASF SE, Ludwigshafen (DE)

( * ) Notice: Subject to any disclaimer, the term of this patent is extended or adjusted under 35 U.S.C. 154(b) by 313 days.

(21) Appl. No.: 13/376,226

(22) PCT Filed: Jun. 11, 2010

(86) PCT No.: PCT/EP2010/058201
§ 371 (c)(1),
(2), (4) Date: Dec. 5, 2011

(87) PCT Pub. No.: WO2010/145993
PCT Pub. Date: Dec. 23, 2010

(65) Prior Publication Data
US 2012/0076843 A1 Mar. 29, 2012

(30) Foreign Application Priority Data
Jun. 15, 2009 (EP) .................................. 09162662

(51) Int. Cl.
| | | |
|---|---|---|
| B01J 13/14 | (2006.01) | |
| A61K 8/11 | (2006.01) | |
| A61K 8/81 | (2006.01) | |
| C09B 67/02 | (2006.01) | |
| F28D 20/02 | (2006.01) | |

(52) U.S. Cl.
CPC ............ B01J 13/14 (2013.01); *Y10T 428/2989* (2015.01); A61K 8/11 (2013.01); A61K 8/8147 (2013.01); *A61K 2800/412* (2013.01); C09B 67/0097 (2013.01); F28D 20/023 (2013.01); *Y02E 60/145* (2013.01)

(58) Field of Classification Search
CPC ........ B82Y 30/00; B82Y 5/00; A61K 9/0024; A61K 47/34; A61K 9/127; A61K 9/0019; A61K 9/0021; A61K 9/0078; A61K 8/85; A61K 9/146; A61K 2800/54; A61K 8/11; A61K 2800/412; A61K 2800/413; A61K 2800/56; C04B 41/48
See application file for complete search history.

(56) References Cited

U.S. PATENT DOCUMENTS

| | | | |
|---|---|---|---|
| 5,972,508 A * | 10/1999 | Boeckh et al. ............ | 428/402.2 |
| 6,200,681 B1 * | 3/2001 | Jahns et al. .............. | 428/402.24 |
| 8,034,887 B2 | 10/2011 | Jung | |
| 8,449,981 B2 * | 5/2013 | Jung et al. ................ | 428/407 |
| 2004/0197357 A1 | 10/2004 | Heming et al. | |
| 2008/0033075 A1 * | 2/2008 | Schmidt et al. ............. | 523/206 |
| 2008/0166555 A1 | 7/2008 | Lang-Wittkowski et al. | |
| 2008/0318048 A1 | 12/2008 | Amrhein et al. | |
| 2009/0256107 A1 | 10/2009 | Hentze et al. | |
| 2010/0036020 A1 | 2/2010 | Zhao et al. | |
| 2010/0168275 A1 | 7/2010 | Zhao et al. | |
| 2010/0327216 A1 | 12/2010 | Jung et al. | |
| 2011/0003152 A1 | 1/2011 | Grey | |

FOREIGN PATENT DOCUMENTS

| | | |
|---|---|---|
| DE | 10 2005 002 411 | 7/2006 |
| JP | 2000-063513 | 2/2000 |
| JP | 2000063513 A * | 2/2000 |
| JP | 2003-001098 | 1/2003 |
| WF | 2006 092439 | 9/2006 |
| WO | 02 100525 | 12/2002 |
| WO | WO 2005116559 A1 * | 12/2005 |
| WO | 2008 006762 | 1/2008 |
| WO | 2008 058868 | 5/2008 |
| WO | 2008 064999 | 6/2008 |
| WO | WO 2008071649 A2 * | 6/2008 |
| WO | 2008 151941 | 12/2008 |

OTHER PUBLICATIONS

International Search Report Issued Jan. 27, 2011 in PCT/EP10/058201 Filed Jun. 11, 2010.
U.S. Appl. No. 13/372,864, filed Feb. 14, 2012, Schroeder-Grimonpont, et al.
U.S. Appl. No. 13/499,502, filed Mar. 30, 2012, Willax, et al.
U.S. Appl. No. 13/383,334, filed Jan. 10, 2012, Jung, et al.

* cited by examiner

*Primary Examiner* — Isis Ghali
(74) *Attorney, Agent, or Firm* — Oblon, McClelland, Maier & Neustadt, L.L.P.

(57) ABSTRACT

The present invention relates to microcapsules comprising a capsule core and a capsule wall, obtainable by a process comprising the free-radical polymerization of an oil-in-water emulsion which comprises the following constituents:

30 to 90% by weight based on the total weight of the monomers of one or more monomers (monomers I) from the group comprising $C_1$-$C_{24}$-alkyl esters of acrylic acid and/or methacrylic acid, acrylic acid, methacrylic acid, maleic acid, fumaric acid and itaconic acid 10 to 70% by weight based on the total weight of the monomers of one or more ethylenically unsaturated crosslinkers (monomers II), where at least 10% by weight, based on the total weight of the monomers I, II and III, is a highly branched polymeric crosslinker, 0 to 30% by weight based on the total weight of the monomers of one or more monounsaturated monomers (monomer III), which are different from the monomers I, and a hydrophobic core material, to a process for their preparation and to their use.

21 Claims, No Drawings ically, it was an object of the present invention to
HIGHLY BRANCHED POLYMERS AS CROSS-LINKING AGENTS IN MICROCAPSULE WALL The present invention relates to microcapsules comprising a capsule core and a capsule wall, obtainable by a process comprising the free-radical polymerization of an oil-in-water emulsion which comprises the following constituents:

| | |
|---|---|
| 30 to 90% by weight | based on the total weight of the monomers of one or more monomers (monomers I) from the group comprising $C_1$-$C_{24}$-alkyl esters of acrylic acid and/or methacrylic acid, acrylic acid, methacrylic acid, maleic acid, fumaric acid and itaconic acid |
| 10 to 70% by weight | based on the total weight of the monomers of one or more ethylenically unsaturated crosslinkers (monomers II), where at least 10% by weight, based on the total weight of the monomers I, II and III, is a highly branched polymeric crosslinker, |
| 0 to 30% by weight | based on the total weight of the monomers of one or more monounsaturated monomers (monomer III), which are different from the monomers I, and a hydrophobic core material. |

The present invention also relates to processes for their preparation and to their use.

Microcapsules are known in highly diverse forms and are used for very different purposes depending on the tightness of the capsule wall. For example, they serve to protect core materials. Microcapsules of this type comprise, for example, latent heat storage materials, often also referred to as PCM (phase change material), the mode of function of which is based on the fact that the solid/liquid phase transition signifies, on account of the enthalpy of transition, an energy absorption or energy discharge to the surrounding area. They can therefore be used for keeping the temperature constant within a fixed temperature range.

In addition, core materials are known which are to be released only as a result of targeted mechanical destruction of the capsule wall, such as dyes for copy papers or encapsulated fragrances.

Furthermore, materials are known which are released in a delayed manner for example through diffusion from the microcapsules, for example biocides.

In the aforementioned fields of application, capsule wall materials based on gelatin, polyurethane and polyurea and also based on polyacrylates and polymethacrylates are known.

In recent years, there have been diverse developments in the field of microencapsulated latent heat storage materials. For example, EP-A-1 029 018 and EP-A 1 321 182 teach the use of microcapsules with a capsule wall of highly crosslinked methacrylic acid ester polymer and a latent heat storage core in binding construction materials such as concrete or gypsum. Furthermore, WO 2008/071649 describes microcapsules based on methacrylic acid esters and a crosslinker combination of butanediol diacrylate and pentaerythritol tetraacrylate.

A general requirement for microcapsule dispersions is good rheology. Microcapsule dispersions should exhibit good flowability even under shear.

In addition, microcapsule dispersions are desired which have a high solids fraction, thus the fraction of the core material, which after all determines the effect of the capsule, is higher. Microcapsule dispersions with high solids contents are obtainable neither by isolation of the microcapsules and subsequent redispersion nor directly from the microencapsulation process itself. As a rule, attempts to prepare microcapsule dispersions with a relatively high solids content result in the coagulation of the reaction mixture.

Accordingly, it was an object of the present invention to provide microcapsule dispersions which can also be prepared with a relatively high solids content. The preparation of microcapsule dispersions with high solids contents should here be possible directly from the microencapsulation. In addition, the microcapsule dispersions should generally have improved rheology.

Accordingly, the aforementioned microcapsules have been found. The present application further relates to processes for the preparation of the microcapsules and to their use for copy papers, in cosmetics, in chemical synthesis, in crop protection, as crosslinkers in adhesives, paints, surface coatings, paper coating slips or other coating or impregnation compositions, and also as latent heat storage materials.

Within the context of the present invention, the expression alkyl comprises straight-chain and branched alkyl groups. Suitable short-chain alkyl groups are, for example, straight-chain or branched $C_1$-$C_7$-alkyl groups, preferably $C_1$-$C_6$-alkyl groups and particularly preferably $C_1$-$C_4$-alkyl groups. These include in particular methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl etc.

Suitable longer-chain $C_8$-$C_{20}$-alkyl groups are straight-chain and branched alkyl groups. These are preferably predominantly linear alkyl radicals, as also occur in natural or synthetic fatty acids and fatty alcohols, and oxo alcohols. These include, for example, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl etc. The expression alkyl comprises unsubstituted and substituted alkyl radicals.

The above statements relating to alkyl are also applicable for the alkyl moieties in arylalkyl. Preferred arylalkyl radicals are benzyl and phenylethyl.

Within the context of the present invention, the expression alkylene is straight-chain or branched alkanediyl groups having 1 to 7 carbon atoms, e.g. methylene, 1,2-ethylene, 1,3-propylene, etc.

Cycloalkyl is preferably $C_5$-$C_7$-cycloalkyl, such as cyclopentyl, cyclohexyl or cycloheptyl.

Within the context of the present invention, the expression aryl comprises mono- or polynuclear aromatic hydrocarbon radicals which may be unsubstituted or substituted. The expression aryl is preferably phenyl, tolyl, xylyl, mesityl, duryl, naphthyl, fluorenyl, anthracenyl, phenanthrenyl or naphthyl, particularly preferably phenyl or naphthyl, where, in the case of a substitution, these aryl groups can generally bear 1, 2, 3, 4 or 5, preferably 1, 2 or 3, substituents.

The microcapsules according to the invention comprise a capsule core and a capsule wall. The capsule core consists predominantly, to more than 95% by weight, of core material. The average particle size of the capsules (number-average by means of light scattering) is 1 to 50 μm. According to one preferred embodiment, the average particle size of the capsules is 1.5 to 20 μm. Here, preferably 90% of the particles have a particle size (diameter) D[v, 0.9]≤20 μm. The span value (D[v, 0.9]−D[v, 0.1])/D[v, 0.5] of the microcapsule distribution is preferably 0.1 to 1.5, in particular 0.2 to 1.3.

According to a further preferred embodiment, which results from the preparation of microcapsule dispersion with solids content≥0.55% by weight, the average particle size of the capsules is 1.5 to 10 µm, preferably 2 to 6 µm. The span value (D[v, 0.9]−D[v, 0.1])/D[v, 0.5] of the microcapsule distribution is preferably 0.1 to 1.5, in particular 0.1 to 1.2.

The weight ratio of capsule core to capsule wall is generally from 50:50 to 95:5. Preference is given to a core/wall ratio of 70:30 to 93:7.

Suitable monomers I are $C_1$-$C_{24}$-alkyl esters of acrylic acid and/or methacrylic acid and also the unsaturated $C_3$- and $C_4$-carboxylic acids such as acrylic acid, methacrylic acid, and also maleic acid, fumaric cid and itaconic acid. Suitable monomers I are isopropyl, isobutyl, sec-butyl and tert-butyl acrylate and the corresponding methacrylates, and also particularly preferably methyl, ethyl, n-propyl and n-butyl acrylate and the corresponding methacrylates. In general, the methacrylates and methacrylic acid are preferred.

According to the invention, one or more highly branched polymeric crosslinkers are used as monomer II.

Within the context of the invention, the highly branched polymers on which the crosslinkers are based include star polymers, dendrimers and highly branched polymers different therefrom, such as specifically hyperbranched polymers, which in each case have ethylenically unsaturated groups, usually end groups, and also optionally side groups.

Star polymers are polymers in which three or more chains emerge from one center. The center here may be an individual atom or an atomic group.

Dendrimers are derived structurally from the star polymers, although the individual chains are in each case for their part branched in a stellate manner. They are formed starting from small molecules, onto which monomers carrying a branching unit are added via a continually repeating defined reaction sequence. Thus, with each reaction step, the number of monomer end groups grows, with an ideally spherical, tree structure forming at the end. One characteristic feature of the dendrimers is the number of reaction stages (generations) carried out for their construction. On account of their uniform structure (ideally all of the branches comprise exactly the same number of monomer units), dendrimers are substantially monodisperse, i.e. they generally have a defined molar mass. molecularly and structurally uniform highly branched polymers are referred to below also uniformly as dendrimers.

Within the context of this invention, "hyperbranched polymers" are highly branched polymers which, in contrast to the aforementioned dendrimers, are both molecularly and also structurally nonuniform. They have side chains and/or side branches of differing length and branching and also a molar mass distribution. The width of the molar mass distribution is preferably characterized by a value for the polydispersity (quotient of weight-average molecular weight $M_w$ and number-average molecular weight $M_n$) and is preferably at least 1.1, in particular at least 1.2 and is preferably in the range from 1.1 to 50, preferably from 1.2 to 40, particularly preferably from 1.3 to 30 and very particularly preferably from 1.5 to 10.

The highly branched polymers used according to the invention preferably have a degree of branching (DB) per molecule of from 10 to 100%, preferably 10 to 90% and in particular 10 to 80%. The degree of branching DB is defined here as DB (%)=(T+Z)/(T+Z+L)×100, where T is the average number of the terminally bonded monomer units, Z is the average number of monomer units forming branches, L is the average number of linearly bonded monomer units.

Dendrimers generally have a degree of branching DB of at least >95%, in particular 99%, specifically 99.9 to 100%. Hyperbranched polymers preferably have a degree of branching DB of from 10 to 95%, preferably 25 to 90% and in particular 30 to 80%.

According to the invention, the crosslinkers used are dendrimers and also hyperbranched polymers, where hyperbranched polymers are preferred as crosslinkers since they are generally easier and thus more economical to prepare. Thus, the basic backbones of hyperbranched polymers can often be prepared by single-stage syntheses. For their synthesis, different synthetic approaches are differentiated (C. Gao, D. Yan, Prog. Polym. Sci. 29 (2004), 183-275).

Within the context of this invention, the expressions "highly branched polymeric crosslinker" and in particular "hyperbranched polymeric crosslinker" refer quite generally to polymers which are characterized by a highly branched structure and which carry ethylenically unsaturated groups, usually end groups and/or side groups. Furthermore, they preferably have high functionality. Functionality is to be understood as meaning both the ethylenically unsaturated end groups and side groups and also functional end groups or side groups which are not ethylenically unsaturated. The functional end groups and side groups are dependent on the polymer backbone and ultimately originate from the starting materials or their reaction products. For example, within the context of this invention, a highly functional polycarbonate is to be understood as meaning a product which, besides the carbonate groups which form the polymer backbone, has terminal or lateral functional radicals, which are carbonate groups, carbamoyl chloride groups and/or OH groups and also comprise ethylenically unsaturated groups. Higher functionality is to be understood here as meaning that the polymers have two or more ethylenically unsaturated end groups and/or side groups and also in total at least three, preferably at least six, functional end groups and/or side groups. For the general definition of highly branched polymers, reference is also made to P. J. Flory, J. Am. Chem. Soc. 1952, 74, 2718, and H. Frey et al., Chem. Eur. J. 2000, 6, No. 14, 2499 (in contrast to the naming chosen here, referred to therein as "hyperbranched polymers").

The number of ethylenically unsaturated end groups and/or side groups of the polymeric crosslinker is on average (number-average) at least 2, in particular at least 3.

The maximum number of these radicals is often not more than 100. It can be determined analytically, for example by iodine number determination. Preference is given to polymeric crosslinkers whose functionality is 3 to 50. Preference is given to polymeric crosslinkers whose number of ethylenically unsaturated end groups and/or side groups is 2 to 10.

The double bond content of the hyperbranched polymeric crosslinkers is 0.1 to 10, preferably 0.2 to 8, particularly preferably 0.3 to 6 mol/kg (can be determined via the iodine number).

Preference is given to hyperbranched polymeric crosslinkers which have a weight-average molecular weight $M_w$ in the range from about 800 to 300 000, particularly preferably from 1000 to 100 000 and in particular from 1000 to 80 000 g/mol. The molar mass determination can take place here by gel permeation chromatography with a standard, such as polymethyl methacrylate. The number-average molecular weight Mn is preferably in the region of at least 500, preferably at least 600 and particularly preferably from 750 g/mol to 100

000 g/mol. It is particularly preferably not more than 80 000 and very particularly preferably not more than 30 000 g/mol.

Suitable highly branched polymers are in principle those which are obtainable by polycondensation or polyaddition. Preference is given to using highly branched polymeric crosslinkers whose polymeric basic backbone is constructed by polyaddition or polycondensation—the highly branched polymeric crosslinker is thus a polyaddition product or a polycondensation product.

Polycondensation is understood here as meaning the repeated chemical reaction of functional compounds with suitable reactive compounds with the elimination of low molecular weight compounds, such as water, alcohols, amines, HCl, etc. Polyaddition is understood here as meaning the repeated chemical reaction of functional compounds with suitable reactive compounds without the elimination of low molecular weight compounds.

Suitable polymeric basic backbones have linking groups which are preferably selected from ether groups, ester groups, carbonate groups, amino groups, amide groups, urethane groups and urea groups.

In particular, highly branched crosslinkers that can be used are polymers from the class of polycarbonates, polyesters, polyethers, polyurethanes, polyureas, polyamides, and mixed forms thereof, such as poly(urea urethanes), poly(ether amines), poly(ester amines), poly(ether amides), poly(ester amides), poly(amido amines), poly(ester carbonates), poly(ether carbonates), poly(ether esters) and poly(ether ester carbonates) etc.

Process for the preparation of the basic backbones of the hyperbranched polymers are described in the documents below, to which reference is made in their entirety:
  highly branched and specifically hyperbranched polycarbonates according to WO 2005/026234,
  hyperbranched polyesters according WO 01/46296, DE 101 63 163, DE 102 19 508, DE 102 40 817 or WO 00/64975
  hyperbranched polyethers according to WO 03/062306, WO 00/56802, DE 102 11 664 or DE 199 47 631,
  hyperbranched nitrogen-atom-containing polymers (specifically polyurethanes, polyureas, polyamides, poly(ester amides), poly(ester amines), as described in WO 2006/087227,
  hyperbranched polyurethanes according to WO 97/02304 or DE 199 04 444, WO 2002/081071,
  hyperbranched poly(urea urethanes) according to WO97/02304 or DE 199 04 444,
  hyperbranched polyureas as described in WO 03/066702, WO 2005/044897 and WO 2005/075541,
  hyperbranched amino-group-containing polymers, specifically poly(ester amines) according to WO 2005/007726,
  hyperbranched poly(ester amides) according to WO 99/16810 or EP 1 036 106,
  hyperbranched polyamides, as described in WO 2006/018125,
  hyperbranched poly(ester carbonates) as described in WO 2006/089940.

The modification of highly branched polymers with ethylenically unsaturated groups is likewise known to the person skilled in the art and is described, for example, in WO 2002/081071, to which reference is expressly made.

The insertion of the ethylenically unsaturated groups can take place as early as during the polyaddition or polycondensation by, in addition to the polyfunctional compounds, adding a compound with one or more identical functionality and at least one ethylenically unsaturated radical.

Preferably, following the construction of the basic backbone by polycondensation or polyaddition, the ethylenically unsaturated end groups and/or side groups are inserted.

This polymer-analogous modification takes place, depending on the selected basic backbone and thus end groups present, by reaction of compounds reactive with these end groups which carry ethylenically unsaturated radicals.

Preferred ethylenically unsaturated groups of the polymeric crosslinkers are the methacryloyl radical, acryloyl radical, vinyl radical, allyl radical, maleinyl radical, itaconyl radical, in particular the acryloyl radical, methacryloyl radical and the allyl radical.

Depending on the basic backbone and thus end groups present, the modification with ethylenically unsaturated groups takes place by reaction of compounds reactive with these end groups which carry ethylenically unsaturated radicals.

In particular, preferred highly branched crosslinkers are polyesters, polycarbonates and polyurethanes with ethylenically unsaturated end groups and/or side groups.

As crosslinkers according to the invention, preference is given in particular to polycarbonates and polyurethanes with acryloyl radicals, and specifically polycarbonates with acryloyl radicals.

Hyperbranched Polyesters

Of suitability are, for example, hyperbranched polyesters which are obtained by reacting at least one dicarboxylic acid or its halides, in particular chlorides, its anhydrides or its esters, with at least one tri- or polyfunctional alcohol.

In addition, they are obtainable by reacting at least one organic diol with at least one trifunctional or polyfunctional carboxylic acid, or its halides, its symmetrical and asymmetrical anhydrides R—CO—O—CO—R', or its esters R—CO—OR'.

Tri- or polyfunctional alcohols are understood here as meaning three or four or more OH radicals. Tri- and polyfunctional carboxylic acids are understood here as meaning three or four or more COOH radicals or the corresponding acid halide radicals —CO-Hal, anhydride radicals —CO—O—CO—R' or ester radicals —CO—OR'.

The ethylenically unsaturated groups are preferably inserted directly during the construction of the basic backbone. They can be inserted by the alcohol, the acid or derivatives thereof.

According to one embodiment, the hyperbranched polyesters with ethylenically unsaturated radicals can be prepared by reacting
  at least one ethylenically unsaturated di- and/or polycarboxylic acid or the halides, anhydrides or esters originating from the di- and/or polycarboxylic acids, with
  at least one at least di- and/or tri- and/or polyfunctional alcohol
  optionally a further nonethylenically unsaturated dicarboxylic acid and/or its halide, anhydride or ester,
where the quantitative ratio of the OH groups to the carboxyl groups or groups originating therefrom in the reaction mixture is selected such that the condensation products (K) have on average either one OH group and more than one carboxyl group or group originating therefrom or preferably one carboxyl group or group originating therefrom and more than one OH group.

The polyesters are preferably polyesters with hydroxyl end groups. As a rule, polymers which have both hydroxyl end groups and also acid end groups or derivatives thereof are formed. Preference is given to hyperbranched polymers whose fraction of hydroxyl end groups is ≥50%, based on the sum of the end groups.

Ethylenically unsaturated di- and polycarboxylic acids which may be mentioned are ethylenically unsaturated $C_4$-$C_{10}$-di- or polycarboxylic acids, preferably monoethylenically unsaturated $C_4$-$C_{10}$-dicarboxylic acids, such as maleic acid, fumaric acid, itaconic acid, citraconic acid, methylenemalonic acid, metaconic acid. In addition, the halides, anhydrides and esters originating from these acids are suitable, for example maleic anhydride, dimethyl fumarate or diethyl fumarate.

Preferred nonethylenically unsaturated dicarboxylic acids or their halides, anhydrides or esters are, for example, aliphatic linear or branched $C_2$-$C_{24}$-dicarboxylic acids, such as oxalic acid, malonic acid, succinic acid, adipic acid, octanedioic acid, 1,2-, 1,3- or 1,4-cyclohexanedicarboxylic acid or dodecanedioic acid. Also suitable are aromatic $C_5$-$C_{12}$-dicarboxylic acids, such as phthalic acid, isophthalic acid, terephthalic acid or naphthalenedicarboxylic acid.

Suitable tri- and polyfunctional alcohols are the alcohols (B) specified below within the context of the preparation of the hyperbranched polycarbonates. Preferably, alcohol (B) is selected from $C_3$-$C_8$-triols which have been mono- or polyalkoxylated with at least $C_2$-$C_6$-alkylene oxide.

Examples of difunctional alcohols (diols) (B') are those specified below in the context of the prepreparation of the hyperbranched polycarbonates.

According to a further embodiment, the hyperbranched polyesters with ethylenically unsaturated radicals can, for example, be prepared by reacting at least one ethylenically unsaturated difunctional and/or tri- and/or polyfunctional alcohol with at least one di- and/or polycarboxylic acid and/or its halide, anhydride or ester, and optionally a further nonethylenically unsaturated difunctional and/or triand/or polyfunctional alcohol, where the quantitative ratio of the OH groups to the carbonates in the reaction mixture is selected such that the condensation products (K) have on average either one OH group and more than one carboxyl group or group originating therefrom, or preferably one carboxyl group or group originating therefrom and more than one OH group.

Preferred polycarboxylic acids or their halides, anhydrides or esters are, for example, aconitic acid, 1,3,5-cyclohexanetricarboxylic acid, 1,2,4-benzenetricarboxylic acid, 1,3,5-benzenetricarboxylic acid, 1,2,4,5-benzenetetracarboxylic acid (pyromellitic acid), and also mellitic acid and low molecular weight polyacrylic acids.

Preferred ethylenically unsaturated difunctional or tri- or polyfunctional alcohols are divinyl glycol.

Alternatively, hyperbranched polyesters can also be prepared on the basis of the branching monomer dimethylolpropionic acid, in which case the starting point often selected for the polymerization is a "core molecule" such as trimethylolpropane or pentaerythritol. Polyesters of this type are available under the name Boltorn® (Perstorp Specialty Chemicals). Their modification with ethylenically unsaturated radicals is described, for example, in WO 00/64975, to which reference is expressly made.

Hyperbranched Polycarbonates

Hyperbranched polycarbonates are obtainable by reacting at least one organic carbonate (A) with at least one trifunctional or polyfunctional alcohol (B). Polyfunctional alcohol is understood here as meaning four or more OH radicals.

The hyperbranched polycarbonates are prepared, for example, by a) reacting at least one organic carbonate (A) with at least one trifunctional and/or polyfunctional alcohol (B) with elimination of alcohols, b) intermolecular reaction of the condensation products (K) to give a highly functional, hyperbranched polycarbonate, where the quantitative ratio of the OH groups to the carbonates in the reaction mixture is selected such that the condensation products (K) have on average either one carbonate group and more than one OH group or preferably one OH group and more than one carbonate group.

The polycarbonates are preferably polycarbonates with hydroxyl end groups.

According to a preferred embodiment, the modification with ethylenically unsaturated groups takes place c) by reacting the hyperbranched polycarbonate obtained from b) with an ethylenically unsaturated compound reactive with hydroxyl groups or with carbonate groups, and/or, according to further preferred embodiments, d) by adding an ethylenically unsaturated compound reactive with hydroxyl groups or with carbonate groups before or during step a) and/or step b).

The organic carbonates used as starting material for the polycondensations comprise aliphatic, aromatic/aliphatic and aromatic carbonates (A), preferably of the general formula $R^a$—O—(CO)—O—$R^b$, where $R^a$ and $R^b$ are in each case independently of one another selected from straight-chain or branched $C_1$-$C_{20}$-alkyl, arylalkyl, $C_5$-$C_7$-cycloalkyl and $C_6$-$C_{10}$-aryl radicals, where $R^a$ and $R^b$ may also together with the group —O—(CO)—O— be a cyclic carbonate. The radicals $R^a$ and $R^b$ preferably have the same meaning.

As carbonates (A), mention may be made by way of example of ethylene carbonate, 1,2- or 1,3-propylene carbonate, diphenyl carbonate, ditolyl carbonate, dixylyl carbonate, dinaphthyl carbonate, ethylphenyl carbonate, dibenzyl carbonate, dimethyl carbonate, diethyl carbonate, dipropyl carbonate, dibutyl carbonate, diisobutyl carbonate, dipentyl carbonate, dihexyl carbonate, dicyclohexyl carbonate, diheptyl carbonate, dioctyl carbonate, didecyl carbonate or didodecyl carbonate, dialkyl dicarbonates, such as di(tert-butyl)dicarbonate, or dialkyl tricarbonates such as di(tert-butyl)tricarbonate.

Preference is given to using aliphatic carbonates (A), in particular those in which the radicals $R^a$ and $R^b$ comprise 1 to 5 carbon atoms, such as dimethyl carbonate, diethyl carbonate, dipropyl carbonate, dibutyl carbonate or diisobutyl carbonate. The organic carbonates are reacted with at least one tri- or polyfunctional alcohol (B) or mixtures of these alcohols.

The alcohols are aliphatic or aromatic alcohols.

Examples of compounds with at least three OH groups comprise glycerol, trimethylolmethane, trimethylolethane, trimethylolpropane, 1,2,4-butanetriol, tris(hydroxymethyl)amine, tris(hydroxyethyl)amine, tris(hydroxypropyl)amine, pentaerythritol, diglycerol, triglycerol, polyglycerols, bis(trimethylolpropane), tris(hydroxymethyl) isocyanurate, tris(hydroxyethyl) isocyanurate, phloroglucinol, trihydroxytoluene, trihydroxydimethylbenzene, phloroglucides, hexahydroxybenzene, 1,3,5-benzenetrimethanol, 1,1,1-tris(4'-hydroxyphenyl)methane, 1,1,1-tris(4'-hydroxyphenyl)ethane, sugars, such as, for example, glucose, sugar derivatives, tri- or higher functional polyetherols based on tri- or higher functional alcohols and ethylene oxide, propylene oxide or butylene oxide or mixtures thereof, or polyesterols. Here, preference is given to glycerol, trimethylolethane, trimethylolpropane, 1,2,4-butanetriol, pentaerythritol, and polyetherols thereof based on ethylene oxide or propylene oxide.

These polyfunctional alcohols (B) can also be used in a mixture with difunctional alcohols (B'), with the proviso that the average OH functionality of all of the alcohols used together is greater than 2. Examples of suitable compounds with two OH groups comprise ethylene glycol, diethylene glycol, triethylene glycol, 1,2- and 1,3-propanediol, dipropylene glycol, tripropylene glycol, neopentyl glycol, 1,2-, 1,3- and 1,4-butanediol, 1,2-, 1,3- and 1,5-pentanediol, hexanediol, cyclopentanediol, cyclohexanediol, cyclohexanedimethanol, bis(4-hydroxycyclohexyl)methane, bis(4-hydroxycyclohexyl)ethane, 2,2-bis(4-hydroxycyclohexyl)propane, 1,1'-bis(4-hydroxyphenyl)-3,3,5-trimethylcyclohexane, resorcinol, hydroquinone, 4,4"-dihydroxydiphenyl, bis(4-hydroxyphenyl)sulfide, bis(4-hydroxyphenyl)sulfone, bis(hydroxymethyl)benzene, bis(hydroxymethyl)toluene, bis(p-hydroxyphenyl)methane, bis(p-hydroxyphenyl)ethane, 2,2-bis(p-hydroxyphenyl)propane, 1,1-bis(p-hydroxy-phenyl)cyclohexane, dihydroxybenzophenone, difunctional polyetherpolyols based on ethylene oxide, propylene oxide, butylene oxide or mixtures thereof, polytetrahydrofuran, polycaprolactone or polyesterols based on diols and dicarboxylic acids.

As a rule, the amount of the difunctional alcohol(s) (A') is 0 to 80 mol % with regard to the total amount of all of the alcohols (B) and (B') together. Preferably, the amount is 0 to 50 mol %, particularly preferably 0 to 35 mol % and very particularly preferably 0 to 25 mol %.

Ethylenically unsaturated compounds with groups which react with hydroxyl groups are unsaturated carboxylic acids, such as acrylic acid, methacrylic acid, maleic acid, fumaric acid, itaconic acid, unsaturated carbonyl halides, such as acryloyl chloride or methacryloyl chloride and unsaturated carboxylic acid anhydrides such as maleic anhydride, acrylic anhydride or methacrylic anhydride. Here, in general degrees of esterification of 5-90 mol %, preferably 10-50 mol %, based on the number of OH groups in the polycarbonates, are achieved. Ethylenically unsaturated compounds are also allyl halide, vinyl and allyl chloroformates, ethylenically unsaturated isocyanates, such as, for example, isocyanatoalkyl acrylates and methacrylates or dimethylmetaisopropenylbenzyl isocyanate (TMI) from Cytec Industries.

Ethylenically unsaturated groups can likewise be inserted through the addition of unsaturated compounds comprising OH groups before or during the polycondensation reaction. Mention is to be made here of monoesters of α,β-unsaturated carboxylic acids, such as acrylic acid, methacrylic acid, crotonic acid, itaconic acid, fumaric acid, maleic acid, acrylamidoglycolic acid, methacrylamidoglycolic acid, preferably acrylic acid and methacrylic acid, or vinyl ethers with di- or polyols which preferably have 2 to 20 carbon atoms and at least two hydroxyl groups, such as ethylene glycol, diethylene glycol, triethylene glycol, 1,2-propylene glycol, 1,3-propylene glycol, 1,1-dimethyl-1,2-ethanediol, dipropylene glycol, triethylene glycol, tetraethylene glycol, pentaethylene glycol, tripropylene glycol, 1,2-, 1,3- or 1,4-butanediol, 1,5-pentanediol, neopentyl glycol, 1,6-hexanediol, 2-methyl-1,5-pentanediol, 2-ethyl-1,4-butanediol, 1,4-dimethylolcyclohexane, 2,2-bis(4-hydroxycyclohexyl)propane, glycerol, trimethylolethane, trimethylolpropane, trimethylolbutane, pentaerythritol, ditrimethylolpropane, erythritol, sorbitol, poly-THF with a molecular weight between 162 and 2000, poly-1,3-propanediol with a molecular weight between 134 and 400 or polyethylene glycol with a molecular weight between 238 and 458. Furthermore, esters or amides of (meth)acrylic acid with aminoalcohols, e.g. 2-aminoethanol, 2-(methylamino)ethanol, 3-amino-1-propanol, 1-amino-2-propanol or 2-(2-aminoethoxy)ethanol, 2-mercaptoethanol or polyaminoalkanes, such as ethylenediamine or diethylentriamine, or vinylacetic acid can also be used.

Alternatively, polycarbonates with ethylenically unsaturated radicals can be prepared by adding ethylenically unsaturated alcohols such as isoprenol, allyl alcohol or divinyl glycol during the polycondensation reaction.

Hyperbranched Polyurethanes

The polyurethanes are preferably polyurethanes whose end group modification takes place via the reaction of ethylenically unsaturated compound reactive with hydroxyl groups or with isocyanate groups. The construction of the basic backbone generally takes place by reacting a di-, tri- or polyfunctional compound reactive with isocyanate groups, preferably an alcohol and/or aminoalcohol, with a di- and/or polyisocyanate. Polyfunctional reactive compound is understood as meaning a compound with four or more groups reactive with isocyanate. Polyisocyanate is understood as meaning a compound with, on average, more than two, generally with on average 2.1 to five, specifically on average three to four, isocyanate groups.

Through selection of the use amounts and feed materials it is easily possible for the person skilled in the art to control the degree of branching. Furthermore, the reaction can be controlled such that an excess of isocyanate radicals is present which, in the case of the desired molecule size, is modified with ethylenically unsaturated monofunctional monomers or further end groups, thus stopping the polyaddition reaction.

Suitable di- and polyisocyanates are the aliphatic, cycloaliphatic and aromatic isocyanates known from the prior art.

Diisocyanates are those isocyanates which have a functionality of 2, i.e. two isocyanate groups per molecule. Polyisocyanates are those isocyanates which have on average more than 2, preferably on average at least 2.1 NCO groups per molecule.

Preferred di- or polyisocyanates are 2,4- and 2,6-tolylene diisocyanate or mixtures thereof, 2,4'- and 4,4'-diphenylmethane diisocyanate (MDI) or mixtures thereof, the mixtures of monomeric diphenylmethane diisocyanates and polynuclear homologs of diphenylmethane diisocyanate (polymer-MDI), tetramethylene diisocyanate, tetramethylene diisocyanate trimers, hexamethylene diisocyanate, hexamethylene diisocyanate trimers, isophorone diisocyanate trimer, 2,4' and 4,4'-methylenebis(cyclohexyl)diisocyanate, xylylene diisocyanate, tetramethylxylylene diisocyanate, dodecyl diisocyanate, lysine alkyl ester diisocyanate, where alkyl is $C_1$ to $C_{10}$, 2,2,4- or 2,4,4-trimethyl-1,6-hexamethylene diisocyanate, 1,4-diisocyanato-cyclohexane, 1,3- or 1,4-bis(isocyanatomethyl)cyclohexane or 4-isocyanatomethyl-1,8-octamethylene diisocyanate or 3 (or 4), 8 (or 9)-bis(isocyanatomethyl)-tricyclo[5.2.1.02.6]decane isomer mixtures.

Particular preference is given to di- or polyisocyanates such as hexamethylene diisocyanate, 2,4-tolylene diisocyanate (2,4-TDI), 2,4'-diphenylmethane diisocyanate (2,4'-MDI), triisocyanatotoluene, isophorone diisocyanate (IPDI), 2-butyl-2-ethylpentamethylene diisocyanate, 2-isocyanatopropylcyclohexyl isocyanate, 3(4)-isocyanatomethyl-1-methylcyclohexyl isocyanate, 1,4-diisocyanato-4-methylpentane, 2,4'-methylenebis(cyclohexyl)diisocyanate and 4-methylcyclohexane 1,3-diisocyanate.

Furthermore, it is also possible to use, for example, oligo- or polyisocyanates which can be prepared from said di- or triisocyanates or mixtures thereof through linkage by means of urethane, allophanate, urea, biuret, uretdione, amide, isocyanurate, carbodiimide, uretonimine, oxadiazinetrione or iminooxadiazinedione structures. Preference is given to 2,4'- and 4,4'-diphenylmethane diisocyanate, mixtures of diphenylmethane diisocyanates and polynuclear homologs of diphenylmethane diisocyanate (polymer-MDI), 1,3- and 1,4-phenylene diisocyanate, 4-isocyanatomethyl-1,8-octamethylene diisocyanate, hexamethylene diisocyanate, oligomers of hexamethylene diisocyanate or isophorone diisocyanate (IPDI) having isocyanurate, uretdione, urethane, allophanate, iminooxadiazinedione or biuret groups, oligomers of MDI having urethane, allophanate, carbodiimide or uretonimine groups or oligomers of TDI having urethane, allophanate, carbodiimide or uretonimine groups.

Both for the di- and polyisocyanates it is also possible to use mixtures of said isocyanates.

In order to control the degree of branching, monoisocyanates known to the person skilled in the art, such as phenyl isocyanate, o-, m- or p-tolyl isocyanate, naphthyl isocyanat, phenylsulfonyl isocyanate, toluenesulfonyl isocyanate, butyl isocyanate, hexyl isocyanate, cyclohexyl isocyanate, dodecyl isocyanate or stearyl isocyanate are also suitable. Preference is given to adding phenyl isocyanate, toluenesulfonyl isocyanate, cyclohexyl isocyanate or stearyl isocyanate.

The compounds reactive with isocyanate have hydroxyl groups, mercapto groups and/or amino groups. Preference is given to hydroxyl and/or amino groups and particularly preferably hydroxyl groups.

Examples of compounds with at least three groups reactive with isocyanate are glycerol, trimethylolmethane, trimethylolethane, trimethylolpropane, 1,2,4-butanetriol, 1,2,5-pentanetriol, 1,2,6-hexanetriol, 1,2,7-heptanetriol, 1,2,8-octanetriol, 1,2,9-nonanetriol, 1,2,10-decanetriol, tris(2-hydroxyethyl) isocyanurate, tris(hydroxymethyl)-aminomethane, tris(hydroxyethyl)aminomethane, 2-amino-1,3-propanediol, 2-amino-2-methyl-1,3-propanediol, diethanolamine, dipropanolamine, diisopropanolamine, ethanolpropanolamine, bis(aminoethyl)amine, bis(aminopropyl)amine, tris(aminoethyl)amine, tris(aminopropyl)amine, trisaminononane, tris(2-hydroxyethyl) isocyanurate, pentaerythritol, dipentaerythritol, bis(trimethylolpropane), sugar alcohols, such as, for example, sorbitol, mannitol, diglycerol, threitol, erythritol, adonitol (ribitol), arabitol (lyxitol), xylitol, dulcitol (galactitol), maltitol, isomaltitol, or sugars, such as, for example, glucose, tri- or polyfunctional polyetherols based on tri- or polyfunctional starter molecules and ethylene oxide and/or propylene oxide and/or butylene oxide, or amino-group-terminated derivatives thereof, which are generally known as Jeffamine®, or tri- or polyfunctional polyesterols.

Preferred compounds with at least three or more groups reactive with isocyanate are tri- or polyfunctional alcohols. In this connection, glycerol, trimethylolethane, trimethylolpropane, 1,2,4-butanetriol, 1,2,6-hexanetriol, pentaerythritol, polyetherols based on glycerol, trimethylolpropane and pentaerythritol are particularly preferred.

Examples of compounds with two groups reactive with isocyanate are ethylene glycol, diethylene glycol, triethylene glycol, 1,2- and 1,3-propanediol, dipropylene glycol, tripropylene glycol, neopentyl glycol, 1,2-, 1,3- and 1,4-butanediol, 1,2-, 1,3- and 1,5-pentanediol, 1,6-hexanediol, neopentyl glycol hydroxypivalate, propane-1,2-dithiol, butane-1,2-dithiol, mercaptoethanol, mercaptopropanol, mercaptobutanol, ethylenediamine, tolylenediamine, isophoronediamine, cysteamine, ethanolamine, N-methylethanolamine, 1,2- or 1,3-propanolamine, isopropanolamine, 2-(butylamino)ethanol, 2-(cyclohexylamino)ethanol, 2-amino-1-butanol, 2-(2'-aminoethoxy)ethanol or higher alkoxylation products of ammonia, 4-hydroxypiperidine, 1-hydroxyethylpiperazine, aminopropanethiol or difunctional polyether- or polyesterols, and also difunctional polyetheramines, generally known as Jeffamine®. In this connection, ethylene glycol, 1,2- and 1,3-propanediol, 1,2-, 1,3- and 1,4-butanediol, ethanolamine, 1,2-propanolamine, mercaptoethanol, 4-hydroxypiperidine and 1-hydroxyethylpiperazine or polyetherols are particularly preferred.

Furthermore, it is also possible to use mixtures of said compounds.

During the construction of the basic backbone it is necessary to adjust the ratio of di- and/or polyisocyanate to the compounds reactive with isocyanate groups in such a way that the resulting addition product can comprise isocyanate groups and comprises, on average, at least one, preferably more than one, group reactcive with isocyanate.

The modification with ethylenically unsaturated radicals takes place through reaction with compounds carrying ethylenically unsaturated radicals and reactive with isocyanate groups or hydroxyl groups. By way of example, mention may be made of monoesters of α,β-unsaturated carboxylic acids, such as acrylic acid, methacrylic acid, crotonic acid, itaconic acid, fumaric acid, maleic acid, acrylamidoglycolic acid, methacrylamidoglycolic acid, preferably acrylic acid or methacrylic acid, with di- or polyols which preferably have 2 to 20 carbon atoms and at least two hydroxyl groups, such as ethylene glycol, diethylene glycol, triethylene glycol, 1,2-propylene glycol, 1,3-propylene glycol, 1,1-dimethyl-1,2-ethanediol, dipropylene glycol, triethylene glycol, tetraethylene glycol, pentaethylene glycol, tripropylene glycol, 1,2-, 1,3- or 1,4-butanediol, 1,5-pentanediol, neopentyl glycol, 1,6-hexanediol, 2-methyl-1,5-pentanediol, 2-ethyl-1,4-butanediol, 1,4-dimethylolcyclohexane, 2,2-bis(4-hydroxycyclohexyl)propane, glycerol, trimethylolethane, trimethylolpropane, trimethylolbutane, pentaerythritol, ditrimethylolpropane, erythritol, sorbitol, poly-THF with a molecular weight between 162 and 2000, poly-1,3-propanediol with a molecular weight between 134 and 400 or polyethylene glycol with a molecular weight between 238 and 458. Also suitable are the monovinyl and monoallyl ethers of the aforementioned di- and polyols. Furthermore, it is also possible to use esters or amides of (meth)acrylic acid with amino alcohols, e.g. 2-aminoethanol, 2-(methylamino)-ethanol, 3-amino-1-propanol, 1-amino-2-propanol or 2-(2-aminoethoxy)ethanol, 2-mercaptoethanol or polyaminoalkanes, such as ethylenediamine or diethylenetriamine, or vinylacetic acid.

Also suitable as compounds reactive with isocyanate groups and which carry ethylenically unsaturated radicals are amides of ethylenically unsaturated carboxylic acids and amino alcohols. By way of example, mention may be made of hydroxyalkyl(meth)acrylamides, such as N-hydroxymethylacrylamide, N-hydroxymethylmethacrylamide, N-hydroxyethylacrylamide, N-hydroxyethylmeth-acrylamide, 5-hydroxy-3-oxapentyl(meth)acrylamide, N-hydroxyalkylcrotonamides such as N-hydroxymethylcrotonamide or N-hydroxyalkylmaleimides such as N-hydroxyethyl-maleimide.

Ethylenically unsaturated compounds with groups which react with hydroxyl groups are unsaturated carboxylic acids such as acrylic acid, methacrylic acid, maleic acid, fumaric acid, itaconic acid, unsaturated carbonyl halides, such as acryloyl chloride or methacryloyl chloride, and unsaturated carboxylic acid anhydrides, such as maleic anhydride, acrylic anhydride or methacrylic anhydride. Here, generally degrees of esterification of 5-90 mol %, preferably 10-50 mol %, based on the number of OH groups in the polyurethanes, are achieved. Ethylenically unsaturated compounds are also allyl halide, vinyl and allyl chloroformates, ethylenically unsaturated isocyanates, such as, for example, isocyanatoalkyl acrylates and methacrylates or dimethylmetaisopropenylbenzyl isocyanate (TMI) from Cytec Industries.

Preference is given to using 2-hydroxyethyl(meth)acrylate, 2- or 3-hydroxypropyl(meth)acrylate, 1,4-butanediol mono(meth)acrylate, neopentyl glycol mono(meth)acrylate, 1,5-pentanediol mono(meth)acrylate, 1,6-hexanediol mono(meth)acrylate, glycerol mono- and di(meth)acrylate, trimethylolpropane mono- and di(meth)acrylate, pentaerythritol mono-, di- and tri(meth)acrylate and 4-hydroxybutyl vinyl ether, 2-aminoethyl(meth)acrylate, 2-aminopropyl(meth)acrylate, 3-aminopropyl(meth)acrylate, 4-aminobutyl(meth)acrylate, 6-aminohexyl(meth)acrylate, 2-thioethyl(meth)acrylate, 2-aminoethyl(meth)acrylamide, 2-aminopropyl(meth)acrylamide, 3-amino-propyl(meth)acrylamide, 2-hydroxyethyl(meth)acrylamide, 2-hydroxy-propyl(meth)acrylamide or 3-hydroxypropyl(meth)acrylamide. Particular preference is given to 2-hydroxyethyl acrylate, 2-hydroxyethyl methacrylate, 2- or 3-hydroxypropyl acrylate, 1,4-butanediol monoacrylate, 3-(acryloyloxy)-2-hydroxypropyl (meth)acrylate and the monoacrylates of polyethylene glycol of molar mass from 106 to 238.

Particular preference is given to hydroxyethyl acrylate, hydroxymethyl acrylate, pentaerythritol triacrylate, allylamine and diallylamine, in particular diallylamine and hydroxyethyl acrylate.

Also preferred as crosslinkers according to the invention are in particular polyurethanes with acryloyl or allyl radicals.

Together with the one or more highly branched polymeric crosslinkers it is possible to additionally use conventional low molecular weight crosslinkers which carry two or more ethylenically unsaturated radicals. Within the context of this application, low molecular weight is understood as meaning molecular weights<800 g/mol. Preference is given to using low molecular weight crosslinkers having vinyl, allyl, acryloyl and/or methacryloyl groups.

Suitable low molecular weight crosslinkers are, for example, divinylbenzene and divinylcyclohexane and preferably the diesters of diols with acrylic acid or methacrylic acid, also the diallyl and divinyl ethers of these diols. By way of example, mention may be made of ethanediol diacrylate, ethylene glycol dimethacrylate, 1,3-butylene glycol dimethacrylate, diethylene glycol diacrylate, dipropylene glycol diacrylate, methallylmethacrylamide, allyl acrylate and allyl methacrylate. Particular preference is given to propanediol, butanediol, pentanediol and hexanediol diacrylates and the corresponding methacrylates.

Also preferred as low molecular weight crosslinkers are the polyesters of polyols with acrylic acid and/or methacrylic acid, and also the polyallyl and polyvinyl ethers of these polyols. Preference is given to crosslinkers with three and/or 4 free-radically polymerizable double bonds such as trimethylolpropane triacrylate and methacrylate, pentaerythritol triallyl ether, pentaerythritol tetraallyl ether, pentaerythritol triacrylate and pentaerythritol tetraacrylate, and their technical-grade mixtures.

Furthermore, one or more monounsaturated monomers (monomer III), which are different from the monomers I, can be added to the monomer mixture. Suitable monomers III are monounsaturated monomers such as vinyl acetate, vinyl propionate, vinylpyridine and styrene or α-methylstyrene, itaconic acid, vinylphosphonic acid, maleic anhydride, 2-hydroxyethyl acrylate and methacrylate, acrylamido-2-methylpropanesulfonic acid, methacrylonitrile, acrylonitrile, methacrylamide, N-vinylpyrrolidone, N-methylolacrylamide, N-methylolmethacrylamide, dimethylaminoethyl methacrylate and diethylaminoethyl methacrylate. Preferably suitable are monounsaturated monomers (monomers IIIa), such as vinyl acetate, vinyl propionate, vinylpyridine and styrene or α-methylstyrene.

The capsule wall is obtainable by a process comprising the free-radical polymerization of an oil-in-water emulsion which comprises the hydrophobic core material and also the monomers I, II and optionally III. It is assumed here that the wall material is formed by copolymerization of the monomers. However, it is unclear to what extent the highly branched polymeric crosslinker used according to the invention is copolymerized therewith. In this connection, both bonding via one and also more double bonds is conceivable. Moreover, it is conceivable that polymeric crosslinkers are bonded to the wall in a noncovalent manner.

The oil-in-water emulsion comprises generally at least 30% by weight, in a preferred form at least 40% by weight, in a particularly preferred form at least 50% by weight, and also up to 90% by weight, preferably at most 85% by weight and in particular at most 80% by weight of at least one monomer selected from $C_1$-$C_{24}$-alkyl esters of acrylic acid and/or methacrylic acid, acrylic acid, methacrylic acid and maleic acid (monomers I), based on the total weight of the monomers used.

Furthermore, the oil-in-water emulsion comprises at least 10% by weight, preferably at least 15% by weight, preferably at least 20% by weight, and also in general at most 70% by weight, preferably at most 65% by weight and in a particularly preferred form at most 60% by weight, of one or more ethylenically unsaturated crosslinkers (monomers II), based on the total weight of the monomers, where at least 10% by weight, preferably at least 20% by weight, in particular at least 30% by weight and at most 70, preferably at most 60 and in particular at most 55% by weight, based on the total weight of the monomers I, II and III, are highly branched, in particular hyperbranched, polymeric crosslinkers.

In addition, the oil-in-water emulsion can comprise up to 30% by weight, preferably up to 20% by weight, in particular up to 10% by weight, of one or more monounsaturated monomers (monomer III), which are different from the monomers I.

Preferably, the oil-in-water emulsion comprises, as monomers, only those of groups I and II.

Preference is given to microcapsules obtainable by a process comprising the free-radical polymerization of an oil-in-water emulsion which comprises 40 to 70% by weight based on the total weight of the monomers of one or more monomers (monomers I) from the group comprising $C_1$-$C_{24}$-alkyl esters of acrylic acid and/or methacrylic acid, acrylic acid, methacrylic acid, maleic acid, fumaric acid and itaconic acid 30 to 60% by weight based on the total weight of the monomers of one or more ethylenically unsaturated crosslinkers (monomers II), where at least 30% by weight, based on the total weight of the monomers I, II and III, are highly branched polymeric crosslinkers, 0 to 30% by weight based on the total weight of the monomers of one or more monounsaturated monomers (monomer III), which are different from the monomers I, and hydrophobic core material.

These microcapsules still exhibit good tightnesses, especially during the evaporation test at 180° C. Particularly in the case of the preparation of microcapsule dispersions with high solids contents, very good tightnesses of the microcapsules are observed.

The microcapsules according to the invention can be prepared by a so-called in situ polymerization. The principle of microcapsule formation is based on the fact that the monomers, free-radical starter, optionally protective colloid and the core material to be encapsulated are used to prepare an oil-in-water emulsion in which the monomers and the core material are present as disperse phase. Usually, this occurs by preparing the oil phase from the individual components and dispersing the oil phase in the water phase. The polymerization of the monomers is then triggered, usually by heating, and the polymerization is optionally controlled by further increasing the temperature, and the polymers that are produced form the capsule wall which surrounds the core material. This general principle is described, for example, in DE-A-10 139 171, to the contents of which reference is expressly made.

As a rule, the microcapsules are prepared in the presence of at least one organic and/or inorganic protective colloid. Both organic and inorganic protective colloids may be ionic or neutral. Protective colloids can be used here either individually or else in mixtures of two or more identically or differently charged protective colloids.

Inorganic protective colloids are inorganic solid particles so-called Pickering systems. Such a Pickering system can consist here of the solid particles on their own or additionally of auxiliaries which improve the dispersibility of the particles in water or the wettability of the particles by the lipophilic phase. The mode of action and their use is described in EP-A-1 029 018 and EP-A-1 321 182, to the contents of which reference is expressly made.

The inorganic solid particles may be metal salts, such as salts, oxides and hydroxides of calcium, magnesium, iron, zinc, nickel, titanium, aluminum, silicon, barium and manganese. Mention is to be made of magnesium hydroxide, magnesium carbonate, magnesium oxide, calcium oxalate, calcium carbonate, barium carbonate, barium sulfate, titanium dioxide, aluminum oxide, aluminum hydroxide and zinc sulfide. Silicates, bentonite, hydroxyapatite and hydrotalcites may likewise be mentioned. Particular preference is given to $SiO_2$-based silicas, magnesium pyrophosphate and tricalcium phosphate.

Suitable $SiO_2$-based protective colloids are highly disperse silicas. They can be dispersed in water as fine, solid particles. However, it is also possible to use so-called colloidal dispersions of silica in water. Such colloidal dispersions are alkaline, aqueous mixtures of silica. In the alkaline pH range, the particles are swollen and stable in water. For a use of these dispersions as protective colloid it is advantageous if the pH of the oil-in-water emulsion is adjusted to pH 2 to 7 using an acid. Preferred colloidal dispersions of silica have a specific surface area in the range from 70 to 90 $m^2/g$ at pH 9.3.

Preferred $SiO_2$-based protective colloids are highly disperse silicas whose average particle size is in the range from 40 to 150 nm at pH values in the range from 8-11. By way of example, mention may be made of Levasil® 50/50 (H. C. Starck), Köstrosol® 3550 (CWK Bad Köstritz), and Bindzil® 50/80 (Akzo Nobel Chemicals).

Organic protective colloids are preferably water-soluble polymers which lower the surface tension of the water from 73 mN/m maximum to 45 to 70 mN/m and thus ensure the formation of closed capsule walls and also form microcapsules with preferred particle sizes in the range from 0.5 to 50 μm, preferably 0.5 to 30 μm, in particular 0.5 to 10 μm.

Organic anionic protective colloids are sodium alginate, polymethacrylic acid and its copolymers, the copolymers of sulfoethyl acrylate and methacrylate, sulfopropyl acrylate and methacrylate, of N-(sulfoethyl)maleimide, of 2-acrylamido-2-alkylsulfonic acid, styrenesulfonic acid and vinylsulfonic acid. Preferred organically anionic protective colloids are naphthalenesulfonic acid and naphthalenesulfonic acid-formaldehyde condensates and in particular polyacrylic acids and phenolsulfonic acid-formaldehyde condensates.

Organic neutral protective colloids are, for example, cellulose derivatives such as hydroxyethylcellulose, methylhydroxyethylcellulose, methylcellulose and carboxymethylcellulose, polyvinylpyrrolidone, copolymers of vinylpyrrolidone, gelatin, gum arabic, xanthan, casein, polyethylene glycols, polyvinyl alcohol and partially hydrolyzed polyvinyl acetate, and also methylhydroxypropylcellulose. Preferred organic neutral protective colloids are polyvinyl alcohol, partially hydrolyzed polyvinyl acetates, and also methylhydroxy($C_1$-$C_4$)-alkylcellulose, and their mixtures.

Methylhydroxy($C_1$-$C_4$)-alkylcellulose is to be understood as meaning methylhydroxy-($C_1$-$C_4$)-alkylcellulose with highly diverse degrees of methylation and also degrees of alkoxylation.

Methylhydroxy-($C_1$-$C_4$)-alkylcelluloses are prepared in a known manner by two reaction steps. In one step, the alkoxylation of cellulose with alkylene oxides takes place. In the second step, the methylation of hydroxyl groups present takes place with a methyl halide. These two reactions generally take place in succession, but can also be carried out simultaneously. Depending on the stoichiometry of the employed alkylene oxides and alkylating agents relative to the cellulose, the degree of substitution of the cellulose varies. The average degree of substitution (DS) indicates how many hydroxyl units have on average been etherified onto one dehydroglucose unit and can be from 0 to 3. The molar degree of substitution (MS) indicates the average number of alkoxy units per dehydroglucose unit and may also be greater than 3 as a result of the formation of side chains during the alkoxylation.

The preferred methylhydroxy($C_1$-$C_4$)-alkylcelluloses have an average degree of substitution DS of from 1.1 to 2.5 and a molar degree of substitution MS of from 0.03 to 0.9.

Suitable methylhydroxy($C_1$-$C_4$)-alkylcelluloses are, for example, methylhydroxyethylcellulose or methylhydroxypropylcellulose. Particular preference is given to methylhydroxypropylcellulose. Methylhydroxy($C_1$-$C_4$)-alkylcelluloses of this type are available, for example, under the trade names Culminal® from Hercules/Aqualon.

Polyvinyl alcohol is obtainable by polymerizing vinyl acetate, optionally in the presence of comonomers, and hydrolyzing the polyvinyl acetate with the elimination of the acetyl groups to form hydroxyl groups. The degree of hydrolysis of the polymers can be, for example, 1 to 100% and is preferably in the range from 50 to 100%, in particular from 65 to 95%. Within the context of this application, partially hydrolyzed polyvinyl acetates is understood as meaning a degree of hydrolysis of <50% and polyvinyl alcohol is understood as meaning from ≥50 to 100%. The preparation of homopolymers and copolymers of vinyl acetate and the hydrolysis of these polymers with the formation of polymers comprising vinyl alcohol units is generally known. Polymers comprising vinyl alcohol units are sold, for example, as Mowiol® grades by Kuraray Specialities Europe (KSE).

Preference is given to polyvinyl alcohols or partially hydrolyzed polyvinyl acetates whose viscosity of a 4% strength by weight aqueous solution at 20° C. in accordance with DIN 53015 has a value in the range from 3 to 56 mPa*s, preferably a value from 14 to 45 mPa*s, in particular from 22 to 41 mPa*s. Preference is given to polyvinyl alcohols with a degree of hydrolysis of ≥65%, preferably ≥70%, in particular ≥75%. Preferably, the microcapsules according to the invention are only prepared with polyvinyl alcohol and/or partially hydrolyzed polyvinyl acetate and without the addition of further protective colloids.

In general, the protective colloids are used in amounts of from 0.1 to 15% by weight, preferably from 0.5 to 10% by weight, based on the water phase. For inorganic protective colloids, preferably amounts of from 0.5 to 15% by weight, based on the water phase, are selected here. Organic protective colloids are preferably used in amounts of from 0.1 to 10% by weight, based on the water phase of the emulsion.

In general, polyvinyl alcohol or partially hydrolyzed polyvinyl acetate are used in a total amount of at least 3% by weight, preferably from 6 to 8% by weight, based on the microcapsules (without protective colloid). Here, it is possible to add customary protective colloids as specified in WO 2005/116559 in addition to the inventively preferred amount of polyvinyl alcohol or partially hydrolyzed polyvinyl acetate.

Free-radical starters which can be used for the free-radical polymerization reaction are the customary oil-soluble peroxo and azo compounds, expediently in amounts of from 0.2 to 5% by weight, based on the weight of the monomers. In this connection, oil-soluble is to be understood as meaning that the free-radical starter is a constituent of the oil phase in the oil-in-water emulsion where it triggers the polymerization.

Depending on the state of aggregation of the free-radical starter and its solubility behavior, it can be introduced as such, but preferably as solution, emulsion or suspension, through which in particular small quantitative amounts of free-radical starter can be dosed more precisely.

Preferred free-radical starters to be mentioned are tert-butyl peroxoneodecanoate, tert-amyl peroxypivalate, dilauroyl peroxide, tert-amyl peroxy-2-ethylhexanoate, 2,2'-azobis(2,4-dimethyl)valeronitrile, 2,2'-azobis(2-methylbutyronitrile), dibenzoyl peroxide, tert-butyl per-2-ethylhexanoate, ditert-butyl peroxide, tert-butyl hydroperoxide, 2,5-dimethyl-2,5-di(tert-butylperoxy)hexane and cumene hydroperoxide.

Particularly preferred free-radical starters are di(3,5,5-trimethylhexanoyl) peroxide, 4,4'-azobisisobutyronitrile, tert-butyl perpivalate and dimethyl 2,2-azobisisobutyrate. These have a half-life of 10 hours in a temperature range from 30 to 100° C.

Furthermore, it is possible to add regulators known to the person skilled in the art in customary amounts to the polymerization, such as tert-dodecyl mercaptan or ethylhexyl thioglycolate.

As a rule, the polymerization is carried out at 20 to 100° C., preferably at 40 to 95° C. Depending on the desired hydrophobic core material, the oil-in-water emulsion is to be formed at a temperature at which the core material is liquid/oil. Accordingly, it is necessary to select a free-radical starter whose decomposition temperature is above this temperature, and likewise to carry out the polymerization 2 to 50° C. above this temperature, and so free-radical initiators are optionally selected whose decomposition temperature is above the melting point of the hydrophobic core material.

A customary process variant for hydrophobic core material with a melting point up to about 60° C. is a reaction temperature starting at 60° C. which is increased to 85° C. in the course of the reaction. Advantageous free-radical starters have a 10 hour half-life in the range from 45 to 65° C., such as t-butyl perpivalate.

According to a further process variant for hydrophobic core materials with a melting point above 60° C., a temperature program is selected which starts at correspondingly higher reaction temperatures. For starting temperatures around 85° C., preference is given to free-radical starters with a 10 hour half-life in the range from 70 to 90° C., such as t-butyl per-2-ethylhexanoate.

The polymerization is expediently carried out at atmospheric pressure, although it is also possible to work at reduced or slightly increased pressure, for example at a polymerization temperature above 100° C., thus about in the range from 0.5 to 5 bar.

The reaction times for the polymerization are normally 1 to 10 hours, in most cases 2 to 5 hours.

After the actual polymerization reaction, for a conversion of 90 to 99% by weight, it is generally advantageous to arrange for the aqueous microcapsule dispersions to be largely free from odor carriers, such as residual monomers and other volatile organic constituents. This can be achieved in a manner known per se by physical means through distillative removal (in particular via steam distillation) or by stripping off with an inert gas. In addition, it can take place by chemical means, as described in WO 99/24525, advantageously by redox-initiated polymerization, as described in DE-A 44 35 423, DE-A 44 19 518 and DE-A 44 35 422.

In this way, it is possible to prepare microcapsules with an average particle size in the range from 0.5 to 100 µm, it being possible to adjust the particle size in a manner known per se via the shear force, the stirring speed, and its concentration. Preference is given to microcapsules with an average particle size in the range from 0.5 to 50 µm, preferably 0.5 to 30 µm, in particular 1 to 10 µm (number-average by means of light scattering). Furthermore, preference is given to microcapsules with an average particle size in the range from 5 to 20 µm preferably.

Suitable materials for the capsule core are water-insoluble to substantially water-insoluble substances, which are referred to within the context of this application as "hydrophobic core material". Substantially insoluble in water is to be understood here as meaning a solubility of the core material in water of <25 g/l, preferably ≤5 g/l at 25° C. If the core material is a mixture, this can be in the form of a solution or suspension. Core materials with the aforementioned solubility in water are preferably selected from the group comprising aliphatic and aromatic hydrocarbon compounds, saturated or unsaturated $C_6$-$C_{30}$-fatty acids, fatty alcohols, $C_6$-$C_{30}$-fatty amines, $C_4$-$C_{30}$-mono-, $C_4$-$C_{30}$-di- and $C_4$-$C_{30}$-polyesters, primary, secondary or tertiary $C_4$-$C_{30}$-carboxamides, fatty acid esters, natural and synthetic waxes, halogenated hydrocarbons, natural oils, $C_3$-$C_{20}$-ketones, $C_3$-$C_{20}$-aldehydes, crosslinkers, adhesive resins and tackifying resins, fragrances and aroma substances, active compounds, dyes, color formers, catalysts and inhibitors.

By way of example, the following may be mentioned:
a) aliphatic hydrocarbon compounds such as saturated or unsaturated $C_6$-$C_{40}$-hydrocarbons, which are linear or branched, e.g. such as n-hexane, n-heptane, n-octane, n-nonane, n-decane, n-undecane, n-dodecane, n-tetradecane, n-pentadecane, n-hexadecane, n-heptadecane, n-octadecane, n-nonadecane, n-eicosane, n-henicosane, n-docosane, n-tricosane, n-tetracosane, n-pentacosane, n-hexacosane, n-heptacosane, n-octacosane, white oils, and also cyclic hydrocarbons, e.g. cyclohexane, cyclooctane, cyclodecane;
b) aromatic hydrocarbon compounds such as benzene, naphthalene, biphenyl, o- or m-terphenyl, $C_1$-$C_{40}$-alkyl-substituted aromatic hydrocarbons such as dodecylbenzene, tetradecylbenzene, hexadecylbenzene, hexylnaphthalene, decylnaphthalene and diisopropylnaphthalene;
c) saturated or unsaturated $C_6$-$C_{30}$-fatty acids, such as lauric acid, stearic acid, oleic acid or behenic acid, preferably eutectic mixtures of decanoic acid with e.g. myristic acid, palmitic acid or lauric acid;

d) fatty alcohols such as lauryl alcohol, stearyl alcohol, oleyl alcohol, myristyl alcohol, cetyl alcohol, mixtures such a coconut fatty alcohol, and the so-called oxo alcohols, which are obtained by hydroformylation of α-olefins and further reactions;
e) $C_5$-$C_{30}$-fatty amines, such as decylamine, dodecylamine, tetradecylamine or hexadecylamine;
f) $C_4$-$C_{30}$-mono-, $C_4$-$C_{30}$-di- and $C_4$-$C_{30}$-polyesters such as $C_1$-$C_{10}$-alkyl esters of $C_1$-$C_{20}$-carboxylic acids, such as propyl palmitate, methyl stearate or methyl palmitate, and preferably their eutectic mixtures or methyl cinnamate and primary, secondary or tertiary $C_4$-$C_{30}$-carboxamides, such as N,N-dimethyloctanamide and N,N-dimethyldecanamide;
g) natural and synthetic waxes such as montanic acid waxes, montanic ester waxes, carnauba wax, polyethylene wax, oxidized waxes, polyvinyl ether wax, ethylene vinyl acetate wax or hard waxes according to Fischer-Tropsch processes;
h) halogenated hydrocarbons such as chloroparaffin, bromooctadecane, bromopentadecane, bromononadecane, bromoeicosane, bromodocosane;
i) natural oils such as peanut oil and soybean oil;
j) $C_3$-$C_{20}$-ketones and $C_3$-$C_{20}$-aldehydes;
k) crosslinkers optionally as solution in the aforementioned core materials of groups a) to i) and j), such as aziridines, epoxides, oxazolines, isocyanates, oximes, carbodiimides or other reactive polyfunctional compounds such as acids, alcohols, alkoxylates and amines;
l) adhesive resins and tackifying resins, optionally as solution in the aforementioned core materials of groups a) to i), such as epoxy resins, epoxyacrylate resin, polyolefin resins; polyurethane prepolymers, silicone resins, natural and synthetic resins, for example hydrocarbon resins, modified colophony resins, pine and terpene resins;
m) fragrances and aroma substances, optionally as a mixture in the aforementioned core materials of groups a) to i) and j), as described in WO 01/49817, or in "Flavors and Fragrances", Ullmann's Encyclopedia of Industrial Chemistry, Whiley-VCH, 2002, to which reference is expressly made;
n) active compounds such as biocides, active compounds to combat endoparasites and ectoparasites, herbicides, fungicides, algicides, active compounds to combat animal pests e.g. insecticides, acaricides, nematicides, moluscicides and active compounds to combat mites, and also safeners, optionally as a solution or suspension in the aforementioned core materials of groups a) to i) and j), as described in WO 2006/092409;
o) moreover mixtures of dyes and/or color formers, in the aforementioned core materials of groups a) to i) and j);
q) catalysts and inhibitors, optionally as a solution in the aforementioned core materials.

The substances of groups a) to h), preferably of group a), provided they pass through a phase change, preferably a solid/liquid phase change, in the temperature range from −20 to 120° C., are suitable as phase change materials (PCM), also known as latent heat storage materials. Depending on the temperature range in which heat storage is desired, the latent heat storage materials are selected as explained in WO 2006/018130, to which reference is expressly made. Furthermore, mixtures of these substances are suitable provided this does not result in a reduction in the melting point to outside of the desired range, or the heat of melting of the mixture does not become too low for a useful application.

Furthermore, it may be advantageous to add to the core materials compounds soluble therein in order, in so doing, to prevent the crystallization delay which sometimes arises in the case of nonpolar substances. As described in U.S. Pat. No. 5,456,852, compounds are advantageously used as additive which have a melting point that is 20 to 120 K higher than that of the actual core substance. Suitable compounds are the fatty acids, fatty alcohols, fatty amides and aliphatic hydrocarbon compounds mentioned above as core materials. They are added in amounts of from 0.1 to 10% by weight, based on the capsule core.

Preferred latent heat storage materials are aliphatic hydrocarbons so-called paraffins, particularly preferably pure n-alkanes, n-alkanes with a purity greater than 80% or alkane mixtures, as are produced as technical-grade distillate and are commercially available as such. In particular, aliphatic hydrocarbons having 14 to 20 carbon atoms, and mixtures thereof, are preferred.

Furthermore, preferred core materials are adhesive resins for two-component adhesives, crosslinkers for two-component adhesives, fragrances and aroma substances, active compounds, dyes and/or color formers, in each case optionally as solution in the aforementioned core materials of groups a) to i) and j).

The core material is particularly preferably a crosslinker for two-component adhesives or an adhesive resin for two-component adhesives. Preferred adhesive resins are, for example, epoxy resins and epoxy acrylate resins, the starting materials for reactive adhesives.

Epoxy adhesive resins are described in the book by C. A. May "Epoxy resins" second edition, Marcel Dekker, Inc. Suitable epoxy resins are diepoxy or polyepoxy resins, in particular those with an average molecular weight≤5 5000 g/mol. They are available, for example, under the name Araldite® from Huntsmann International LLC. Preference is likewise given to epoxy acrylate resins. Preference is given to resins based on glycidyl acrylates and methacrylates. Preferred starting monomers for these resins are glycidyl acrylate and/or glycidyl methacrylate, acrylates, styrene and also hydroxyalkyl acrylates. Such products are available under the name Joncryl® ADR from BASF Corp.

Preferred crosslinkers k) are di- and polyfunctional amines with primary, secondary or tertiary amino groups which have a solubility in water of <5 g/l at a temperature of 20° C.

Suitable crosslinkers k) are also diepoxides.

Depending on the core material, the microcapsules according to the invention are suitable for copy paper, in cosmetics, for the encapsulation of adhesives, adhesive components, catalysts or in crop protection or generally for the encapsulation of biocides. The microcapsules according to the invention are particularly suitable for latent heat storage materials.

The microcapsules according to the invention can be processed directly as aqueous microcapsule dispersion or in the form of a powder. The microcapsules according to the invention can optionally then be isolated by spray-drying.

The spray-drying of the microcapsule dispersion can take place in the customary manner. In general, the procedure is such that the inlet temperature of the stream of warm air is in the range from 100 to 200° C., preferably 120 to 160° C., and the outlet temperature of the stream of warm air is in the range from 30 to 90° C., preferably 60 to 80° C. The spraying of the aqueous polymer dispersion in the stream of warm air can take place, for example, by means of single-component or multiple-component nozzles or via a rotating disk. Deposition of the polymer powder normally takes place using cyclones or filter separators. The sprayed aqueous polymer dispersion and the stream of warm air are preferably conveyed in parallel.

For the spray-drying, spraying auxiliaries are optionally added in order to facilitate the spray-drying, or to establish certain powder properties, e.g. low dust content, pourability or improved redispersibility. A large number of spraying auxiliaries is known to the person skilled in the art. Examples thereof can be found in DE-A 19629525, DE-A 19629526, DE-A 2214410, DE-A 2445813, EP-A 407889 or EP-A 784449. Advantageous spraying auxiliaries are, for example, water-soluble polymers of the polyvinyl alcohol type or partially hydrolyzed polyvinyl acetates, cellulose derivatives such as hydroxyethylcellulose, carboxymethylcellulose, methylcellulose, methylhydroxyethylcellulose and methylhydroxypropylcellulose, polyvinylpyrrolidone, copolymers of vinylpyrrolidone, gelatin, preferably polyvinyl alcohol and partially hydrolyzed polyvinyl acetates and also methylhydroxypropylcellulose.

The microcapsule dispersions according to the invention can be prepared with a high solids fraction. Thus, solids contents >50% by weight, preferably >55% by weight and in particular up to 60% by weight are possible. Moreover, the microcapsule dispersions according to the invention exhibit advantageous rheology behavior. Thus, even the flowability in the presence of shear forces is improved.

According to one embodiment, microcapsules according to the invention with catalysts and/or inhibitors are suitable as core material in the chemical synthesis or in the polymerization.

Depending on the core material, the microcapsules according to the invention are suitable for copy paper, in cosmetics, for the encapsulation of adhesives, adhesive components, catalysts or in crop protection or generally for the encapsulation of biocides. Microcapsules with core materials of group p) are suitable as crosslinkers in adhesives, paints, surface coatings, paper coating slips or other coating or impregnation compositions.

Furthermore, the microcapsules according to the invention with a capsule core material from groups a) to h), provided it passes through a solid/liquid phase change (PC material) in the range from −20 to 100° C., are suitable as latent heat storage materials. The fields of use of microencapsulated phase change materials are generally known. For example, the microcapsules according to the invention can advantageously be used for modifying fibers and textile products, for example textile fabrics and nonwovens etc. Application forms to be mentioned here are in particular microcapsule coatings, foams with microcapsules and microcapsule-modified textile fibers. For coatings, the microcapsules are applied together with a polymeric binder and optionally other auxiliaries, generally in the form of a dispersion, to a textile product. Customary textile binders are film-forming polymers with a glass transition temperature in the range from −45 to 45° C., preferably −30 to 12° C. The preparation of microcapsule coatings is described, for example in WO 95/34609, to which reference is expressly made. The modification of foams with microcapsules takes place in a similar manner, as described in DE 981576T and U.S. Pat. No. 5,955,188. The prefoamed substrate, preferably a polyurethane or polyether, is surface-treated with a binder-containing microcapsule dispersion. The binder/microcapsule mixture then passes into the open-pore foam structure by applying a vacuum, where the binder hardens and binds the microcapsules to the substrate. A further processing option is the modification of textile fibers themselves, e.g. by spinning from a melt or an aqueous dispersion, as described in US 2002/0054964. Melt spinning methods are used here for nylon fibers, polyester fibers, polypropylene fibers and similar fibers whereas the wet spinning method is used primarily for producing acrylic fibers.

A further broad field of application is binding construction materials with mineral, silicatic or polymeric binders. A distinction is made here between moldings and coating masses.

A mineral molding is understood here as meaning a molding which is formed from a mixture of a mineral binder, water, aggregates, and optionally auxiliaries after molding as a result of the mineral binder/water mixture hardening as a function of time, optionally in the presence of elevated temperature. Mineral binders are generally known. These are finely divided inorganic substances such as lime, gypsum, clay, loam and/or cement, which are converted into their ready-to-use form by stirring with water, the latter, when left by themselves, in the air or else under water, optionally in the presence of elevated temperature, solidifying in a stone-like manner as a function of time.

The aggregates generally consist of granular or fiber-like natural or synthetic stone (gravel, sand, glass fibers or mineral fibers), in special cases also of metals or organic aggregates or of mixtures of said aggregates, having particle sizes or fiber lengths which are adapated to the particular intended use in a manner known per se.

Suitable auxiliaries are in particular those substances which accelerate or delay hardening or which influence the elasticity or porosity of the solidified mineral molding.

The microcapsules according to the invention are suitable for the modification of mineral binding construction materials (mortar-like preparations) which comprise a mineral binder which consists of 70 to 100% by weight of cement and 0 to 30% by weight of gypsum. This is the case particularly if cement is the sole mineral binder, the effect being independent of the type of cement. As regards further details, reference is made to DE-A 196 23 413. The dry compositions of mineral binding construction materials typically comprise, based on the amount of mineral binder, 0.1 to 20% by weight of microcapsules.

Furthermore, the microcapsules according to the invention can be used as additive in mineral coating masses, such as internal or external plaster. Such a plaster for inside is usually composed of gypsum as binder.

Coatings for outside such as external facades or wet rooms can comprise cement (cement plasters), lime or waterglass (mineral or silicate plasters) or plastics dispersions (synthetic resin plasters) as binders together with fillers and optionally pigments for coloring.

In addition, the microcapsules according to the invention with PC materials are suitable for modifying gypsum construction boards. The production of gypsum construction boards with microencapsulated latent heat storage materials (PCM) is generally known and described in EP-A 1 421 243, to which reference is expressly made. They are usually produced by bringing aqueous gypsum slurry, discontinuously or preferably continuously, between two covering layers, such as cardboard sheets based on cellulose, forming boards. Here, instead of cardboard based on cellulose, it is also possible to use alternative, fibrous structures, preferably glass fibers, as double-face coverings for the "gypsum plaster board". The alternative materials can be used as fabric and as so-called "nonwovens", thus as web-like structures. Construction boards of this type are known, for example, from U.S. Pat. No. 4,810,569, U.S. Pat. No. 4,195,110 and U.S. Pat. No. 4,394,411.

Furthermore, the microcapsules according to the invention with PC materials are suitable as additive in polymeric or lignocellulose-containing moldings, such as chipboard or for polymeric coating masses.

In addition, the microcapsule dispersions according to the invention with PC materials are suitable as heat carrier liquid.

Depending on the field of use, further auxiliaries, or in the case of multicomponent adhesives, the customary components, if appropriate also in encapsulated form, can be added to the microcapsule dispersions according to the invention. Auxiliaries may be, for example, slip additives, adhesion promoters, flow agents, film-forming auxiliaries, flame retardants, corrosion inhibitors, waxes, siccatives, matting agents, deaerating agents, thickeners and water-soluble biocides. Substrates coated with microcapsule dispersions of this type are storage-stable, i.e. even after a storage time of several weeks, the coated substrate can be processed with unchanged good properties.

The examples below are intended to illustrate the invention. The percentage data in the examples are percent by weight, unless stated otherwise.

Synthesis of the Hyperbranched Crosslinkers

Abbreviations Used:
TMP=trimethylolpropane
PO=propylene oxide units (propylene glycol units)
EO=ethylene oxide units (ethylene glycol units)
TDI=2,4-tolylene diisocyanate
HDI=hexamethylene diisocyanate Hereinbelow, for example TMP×5.2 PO is understood as meaning the reaction product of 1 mol of trimethylolpropane with 5.2 mol of propylene oxide. Analogously, TMP×3.6 EO is the reaction product of 1 mol of trimethylolpropane with 3.6 mol of ethylene oxide.

The molecular weight determination was carried out by means of gel permeation chromatography (GPC) using a refractometer as detector. The mobile phase used was THF and the standard for determining the molecular weight used was polymethyl methacrylate (PMMA) calibration mixtures with molecular weights in the range from 200 to 217 000 g/mol. Using dimethylacetamide as the mobile phase, the standard used for determining the molecular weight was polymethyl methacrylate (PMMA) calibration mixtures with molecular weights in the range from 500 to 100 000 g/mol.

The double bond content is determined via the iodine number (in accordance with Kaufmann).

The OH number (mg KOH/g) was determined in accordance with DIN 53240, Part 2.

Example Crosslinker 1
Hyperbranched Polyurethane with Acrylate End Groups

In a 1 l four-neck flask fitted with stirrer, dropping device, nitrogen line and internal thermometer, 250 g of TMP×5.2 PO (0.833 mol) were dissolved in 100 g of toluene. At room temperature, 202.5 g of TDI (1.162 mol) were added over a period of 15 min. When addition was complete, the reaction solution was stirred at 30° C. until an NCO content of 7.3% by weight was reached. Over a period of 60 min, 105 g of hydroxyethyl acrylate (0.905 mol) were added until an NCO content of 0% by weight was reached.

The hyperbranched polyurethane could be characterized as follows:
GPC (eluent: THF): $M_n$=1100 g/mol, $M_w$=5630 g/mol
Iodine number 56 g of iodine/100 g of polymer, double bond content: 2.21 mol/kg of polymer
OH number=60 mg of KOH/g of polymer (the measurement was carried out in an 80% strength by weight solution in toluene and converted to 100% polymer).

Example Crosslinker 2
Hyperbranched Polyurethane with Acrylate End Groups

In a 1 l four-neck flask fitted with stirrer, dropping device, nitrogen line and internal thermometer, 250 g (0.833 mol) of TMP×5.2 PO were dissolved in 100 g of toluene and the resulting solution was treated with one drop of dibutyltin laurate. At room temperature, a mixture of 141.8 g (0.814 mol) of TDI and 58.7 g of HDI (0.349 mol) was added over a period of 15 min. When addition was complete, the reaction solution was stirred at 50° C. until an NCO content of 8.0% by weight was reached. Over a period of 50 min, 105.0 g of hydroxyethyl acrylate (0.905 mol) were added until an NCO content of 0% by weight was reached.

The hyperbranched polyurethane could be characterized as follows:
GPC (eluent: THF): $M_n$=1080 g/mol, $M_w$=7700 g/mol
Iodine number 40 g of iodine/100 g of polymer, double bond content: 1.58 mol/kg of polymer
OH number=17.5 mg KOH/g of polymer (the measurement was carried out in an 80% strength by weight solution in toluene and converted to 100% polymer)

Example Crosslinker 3
Hyperbranched Polyurethane with Allyl End Groups

In a 1 l four-neck flask fitted with stirrer, dropping device, nitrogen line and internal thermometer, 250.0 g (0.833 mol) of TMP×5.2 PO were dissolved in 100 g of toluene and the resulting solution was treated with one drop of dibutyltin laurate. At room temperature, 202.5 g (1.162 mol) of TDI were added over a period of 15 min. When addition was complete, the reaction solution was stirred at room temperature until an NCO content of 7.6% by weight was reached. Then, with dry-ice cooling and over a period of 10 minutes, 94.0 g (0.967 mol) of diallylamine were added until an NCO content of 0% by weight was reached.

The hyperbranched polyurethane could be characterized as follows:
GPC (eluent: THF): $M_n$=940 g/mol, $M_w$=1970 g/mol
Iodine number 118 g of iodine/100 g of polymer, double bond content: 4.65 mol/kg of polymer
OH number=235 mg of KOH/g of polymer (the measurement was carried out in an 80% strength by weight solution in toluene and converted to 100% polymer)

Example Crosslinker 4
Hyperbranched Polyurethane with Allyl End Groups

In a 1 l four-neck flask fitted with stirrer, dropping device, nitrogen line and internal thermometer, 200.0 g (0.741 mol) of TMP×3.6 EO were dissolved in 432 g of toluene and the resulting solution was treated with one drop of dibutyltin laurate. At room temperature, 23.0 g (1.332 mol) of TDI were added over a period of 35 min. When addition was complete, the reaction solution was stirred at RT until an NCO content of 5.1% by weight was reached. Then, with dry-ice cooling and over a period of 20 min, 90 g (0.926 mol) of diallylamine were added until an NCO content of 0% by weight was reached.

The hyperbranched polycarbonate could be characterized as follows:
GPC (eluent: THF): $M_n$=1140 g/mol, $M_w$=2600 g/mol.
Iodine number 116 g of iodine/100 g of polymer, double bond content: 4.57 mol/kg of polymer
OH number=122.5 mg of KOH/g of polymer (the measurement was carried out in an 80% strength by weight solution in toluene and converted to 100% polymer)

Example Crosslinker 5
Hyperbranched Polycarbonate with Acrylate End Groups a) In a 2 l four-neck flask fitted with stirrer, reflux condenser, internal thermometer and nitrogen line, 1000 g (2.326 mol) of TMP×5.2 PO and 384.5 g (3.256 mol) of diethyl carbonate were initially introduced and the mixture was adjusted to pH 8.5 by adding potassium hydroxide. The reaction mixture was slowly heated to boiling and the boiling reaction mixture was stirred until the boiling temperature of the reaction mixture had dropped from 135° C. to a constant temperature of 119° C. as a result of the evaporative cooling of the ethanol released. Then, the reflux condenser was replaced by a distillation bridge and the ethanol formed during the reaction was distilled off, during which the temperature of the reaction mixture was increased to 190° C. The ethanol was collected, weighed and the conversion thus ascertained as a percentage compared with the theoretically possible complete conversion. After achieving a conversion of 80% by weight, the reaction mixture was cooled to 100° C. and adjusted to a pH of 6 by adding 85% strength phosphoric acid. The reaction mixture was then heated again to 160° C. and, at this temperature, dry nitrogen was passed through over a period of 3 h in order to remove any residual amounts of monomers still present. The mixture was then cooled to room temperature. The hyperbranched polycarbonate had an OH number of 133 mg KOH/g.

b) In a 2 l four-neck flask fitted with stirrer, water separator, internal thermometer and nitrogen line, 400 g of the polycarbonate obtained according to a) were dissolved in 400 g of cyclohexane. 54.7 g (0.759 mol) of acrylic acid and 1.2 g of hydroquinone monomethyl ether, 0.4 g of 2,6-ditert-butyl-p-cresol, 0.4 g of 97% strength triphenyl phosphite, 0.4 g of 50% strength by weight hypophoshorous acid and 0.01 g of phenothiazine were added to the solution. After adding 2 g of conc. sulfuric acid, the mixture was heated to reflux for 9 hours at 85° C. on the water separator, during which 3.8 g of water were separated off. For the work-up, the reaction solution was washed three times with in each case 300 ml of a 20% strength by weight sodium chloride solution. The organic phases were dried over sodium sulfate, evaporated and dried in vacuo at 80° C.

The hyperbranched polycarbonate could be characterized as follows:
GPC (eluent: THF): $M_n$=2508 g/mol, $M_w$=8945 g/mol
Iodine number 7.6 g of iodine/100 g of polymer, double bond content: 0.3 mol/kg of polymer
OH number=96 mg of KOH/g of polymer.

Example Crosslinker 6
Hyperbranched Polycarbonate with Acrylate End Groups a) In a 2 l four-neck flask fitted with stirrer, reflux condenser, internal thermometer and nitrogen line, 800 g (2.963 mol) of TMP×1.2 PO and 455 g (3.853 mol) of diethyl carbonate were initially introduced and the mixture was adjusted to pH 9 by adding potassium hydroxide. The reaction mixture was slowly heated to reflux and the boiling reaction mixture was stirred until the boiling temperature of the reaction mixture had dropped from 126° C. to a temperature of 104° C. The reflux condenser was then replaced by a distillation bridge and the ethanol which formed during the reaction was distilled off, during which the temperature of the reaction mixture was increased to 190° C. The ethanol was collected, weighed and the conversion thus ascertained as a percentage compared with the theoretically possible complete conversion. After achieving a conversion of 80% (283 g of ethanol), the reaction mixture was cooled to 100° C. and adjusted to a pH of 6 by adding 85% strength phosphoric acid. The reaction mixture was then heated again to 160° C. and, at this temperature, dry nitrogen was passed through over a period of 3 h in order to remove residual amounts of monomer still present. The mixture was then cooled to room temperature. The hyperbranched polycarbonate had an OH number of 183 mg KOH/g.

b) In a 2 l four-neck flask fitted with stirrer, water separator, internal thermometer and nitrogen line, 400 g of the polycarbonate obtained from a) were dissolved in 400 g of cyclohexane. 75.0 g (1.040 mol) of acrylic acid, 1.2 g of hydroquinone monomethyl ether, 0.4 g of 2,6-ditert-butyl-p-cresol, 0.4 g of 97% strength triphenyl phosphite, 0.4 g of 50% strength hypophosphorous acid and 0.01 g of phenothiazine were added to the solution. After adding 2 g of conc. sulfuric acid as catalyst, the mixture was heated at reflux for 9 h at 85° C. on the water separator, during which 10.9 g of water were separated off. For the work-up, the reaction solution was washed three times with in each case 300 ml of 30% strength by weight sodium chloride solution. The organic phases were dried over sodium sulfate, concentrated by evaporation and dried in vacuo at 80° C.

The hyperbranched polycarbonate could be characterized as follows:
GPC (eluent: THF): Mn=1819 g/mol, Mw=5972 g/mol
Iodine number 17 g of iodine/100 g of polymer, double bond content: 0.67 mol/kg of polymer
OH number=104 mg of KOH/g of polymer Example Crosslinker 7
Hyperbranched Polyester of Maleic Anhydride In a 1 l four-neck flask fitted with stirrer, nitrogen line, distillation device and internal thermometer, 117.7 g of maleic anhydride (1.200 mol) and 430.1 g of TMP×5.2 PO (1.000 mol) were treated with 0.18 g of dibutyltin dilaurate and heated to 160° C. The reaction mixture was stirred at this temperature over a period of 4.5 hours, during which 2.8 g of water were distilled off. The reaction mixture was ended by cooling to room temperature.

The hyperbranched polyester could be characterized as follows:
GPC (eluent: THF): $M_n$=1130 g/mol, $M_w$=6370 g/mol
Acid number=68 mg of KOH/g of polymer, OH number=154 mg of KOH/g of polymer
Double bond content (calculated from the amount of maleic anhydride used per mixture): 2.2 mol/kg of polymer Example Crosslinker 8
Hyperbranched Polyester of Maleic Anhydride In a 4 l four-neck flask fitted with stirrer, nitrogen line, distillation device and internal thermometer, 471.1 g of maleic anhydride (4.804 mol), 724.2 g of succinic anhydride (7.237 mol) and 1016.3 g of glycerol (11.035 mol) were treated with 0.7 g of dibutyltin dilaurate and heated to 160° C. The reaction mixture was stirred at this temperature over a period of 7 h, during which 81 g of water were distilled off. The reaction mixture was ended by cooling to room temperature.

The hyperbranched polyester could be characterized as follows:
GPC (eluent: THF): $M_n$=1900 g/mol, $M_w$=5640 g/mol
Acid number=122 mg of KOH/g of polymer, OH number=390 mg of KOH/g of polymer
Double bond content (calculated from the amount of maleic anhydride used per mixture): 2.2 mol/kg of polymer Example Crosslinker 9
Hyperbranched Polyester of Maleic Anhydride In a 4 l four-neck flask fitted with stirrer, nitrogen line, distillation device and internal thermometer, 113.2 g of maleic anhydride (1.154 mol), 166.6 g of sebacic acid (0.824 mol) and 220.6 g of TMP (1.640 mol) were treated with 0.15 g of dibutyltin dilaurate and heated to 160° C. The reaction mixture was stirred at this temperature over a period of 2 h, during which 7.8 g of water were distilled off. The reaction mixture was ended by cooling to room temperature.

The hyperbranched polyester could be characterized as follows:
GPC (eluent: THF): $M_n$=1140 g/mol, $M_m$=5090 g/mol
Acid number=82 mg of KOH/g of polymer, OH number=295 mg of KOH/g of polymer
Double bond content (calculated from the amount of maleic anhydride used per mixture): 2.3 mol/kg of polymer.

Preparation of the Microcapsule Dispersion

The particle size of the microcapsule powder was determined using a Malvern Particle Sizer model 3600E in accordance with a standard measurement method which is documented in the literature. The D[v, 0.1] value implies that 10% of the particles have a particle size (according to the volume average) up to this value. Accordingly, D[v, 0.5] means that 50% of the particles and D[v, 0.9] that 90% of the particles have a particle size (according to the volume average) less than or equal to this value. The span value is given by the quotient from the difference D[v, 0.9]–D[v, 0.1]) and D[v, 0.5].

Determination of the Evaporation Rate

For the pretreatment, 1 to 2 g of the microcapsule dispersion were dried in a small metal dish for two hours at 105° C. in order to remove any residual water. The weight ($m_o$) was then determined. After heating for one hour at 180° C. and after cooling, the weight ($m_1$) is determined again. The weight difference ($m_0$–$m_1$) based on $m_0$ and multiplied by 100 gives the evaporation rate in %. The lower the value, the tighter the microcapsules. In this connection, it must be ensured that comparisons in the evaporation rate should always be carried out on comparable capsule sizes and stabilizer systems.

Rheology Measurements

The rheology measurements were carried out using a cylinder measurement system (CC 27) on an automatic sample changer (ASC) with a measuring head DSR 301 from Anton Paar. The viscosity was recorded as a function of the shear rate in the range from 25 $s^{-1}$ to 500 $s^{-1}$. In order to be able to report on the time-dependent flow behavior of the samples, measurements were made from low to high shear rates and back again to low shear rates.

Example 1

Not According to the Invention

| Water phase | |
|---|---|
| 291.40 g | of dem. water (dem. = completely demineralized water) |
| 145.50 g | of a 5% strength by weight aqueous solution of methylhydroxypropylcellulose (Culminal ® MHPC 100, Hercules Doel) |
| 36.38 g | of a 10% strength by weight aqueous solution of polyvinyl alcohol (Mowiol ® 15-79, Kuraray) |
| 1.50 g | of a 2.5% strength by weight aqueous solution of sodium nitrite |
| Feed 1 | |
| 330.53 g | of octadecane |
| 6.90 g | of paraffin with a melting point in the range from 65-75° C. |
| Feed 2 | |
| 15.04 g | of methyl methacrylate |
| 15.04 g | of 1,4-butanediol diacrylate |
| 7.50 g | of methacrylic acid |
| Feed 3 | |
| 0.55 g | of a 75% strength by weight solution of tert-butyl perpivalate in aliphatic hydrocarbons |
| Feed 4 | |
| 4.13 g | of a 10% strength by weight aqueous solution of tert-butyl hydroperoxide |
| Feed 5 | |
| 21.71 g | of a 1.06% strength by weight aqueous solution of ascorbic acid. | a) The water phase was poured into a dispersing reactor and heated to 40° C. Feeds 1 and 2 were heated and then added to the water phase. This mixture was then dispersed using a high-speed dissolver stirrer at 3500 rpm and 40° C. After dispersion for 40 minutes, a stable emulsion was obtained.

b) The emulsion was heated to 70° C. with stirring using an anchor stirrer following the metered addition of feed 3 over a period of 60 minutes, heated to a temperature of 85° C. over the course of a further 60 minutes and held at this temperature for one hour. Feeds 4 and 5 were then metered in one after the other. The mixture was then cooled to room temperature over a period of 90 minutes.

This gave a dispersion with a solids content of 43.4% by weight, an average particle size of D[v, 0.5]=5.3 μm (number-average determined by means of light scattering) and an evaporation rate of 8.4%.

Example 2

Not According to the Invention

| Water phase | |
|---|---|
| 249.88 g | of dem. water (dem. = completely demineralized water) |
| 142.30 g | of a 10% strength by weight aqueous solution of polyvinyl alcohol (Mowiol 18-88, Kuraray) |
| 1.96 g | of a 2.5% strength by weight aqueous solution of sodium nitrite |
| Feed 1 | |
| 431.00 g | of octadecane |
| 9.00 g | of paraffin with a melting point in the range from 65-75° C. |
| Feed 2 | |
| 19.61 g | of methyl methacrylate |
| 19.61 g | of 1,4-butanediol diacrylate |
| 9.78 g | of methacrylic acid |
| Feed 3 | |
| 0.72 g | of a 75% strength by weight solution of tert-butyl perpivalate in aliphatic hydrocarbons |
| Feed 4 | |
| 5.38 g | of a 10% strength by weight aqueous solution of tert-butyl hydroperoxide |
| Feed 5 | |
| 28.31 g | of a 1.02% strength by weight aqueous solution of ascorbic acid |

An emulsion was prepared and polymerized analogously to Example 1. This gave a dispersion with a solids content of 55.3% by weight, an average particle size of D[v, 0.5]=3.7 μm (number-average determined by means of light scattering) and an evaporation rate of 8.0%.

Example 3

Not According to the Invention

| Water phase | |
|---|---|
| 159.58 g | of dem. water |
| 130.95 g | of a 10% strength by weight aqueous solution of polyvinyl alcohol (Mowiol 18-88, Kuraray) |
| 1.80 g | of a 2.5% strength by weight aqueous solution of sodium nitrite |
| Feed 1 | |
| 396.63 g | of octadecane |
| 8.28 g | of paraffin with a melting point in the range from 65-75° C. |

-continued

| | Feed 2 | |
|---|---|---|
| 18.05 g | of methyl methacrylate | |
| 18.05 g | of 1,4-butanediol diacrylate | |
| 9.00 g | of methacrylic acid | |
| | Feed 3 | |
| 0.66 g | of a 75% strength by weight solution of tert-butyl perpivalate in aliphatic hydrocarbons | |
| | Feed 4 | |
| 4.95 g | of a 10% strength by weight aqueous solution of tert-butyl hydroperoxide | |
| | Feed 5 | |
| 26.06 g | of a 1.04% strength by weight aqueous solution of ascorbic acid | |

An emulsion was prepared and polymerized analogously to Example 1.

No dispersion could be obtained since the product became solid upon heating to 75° C.

Example 4

| | Water phase | |
|---|---|---|
| 380.00 g | of dem. water | |
| 190.00 g | of a 5% strength by weight aqueous solution of methylhydroxypropylcellulose (Culminal MHPC 100, Hercules Doel) | |
| 47.50 g | of a 10% strength by weight aqueous solution of polyvinyl alcohol (Mowiol 15-79, Kuraray) | |
| 2.10 g | of a 2.5% strength by weight aqueous solution of sodium nitrite | |
| | Feed 1 | |
| 431.00 g | of octadecane | |
| 9.00 g | of paraffin with a melting point in the range from 65-75° C. | |
| | Feed 2 | |
| 19.60 g | of methyl methacrylate | |
| 19.60 g | of crosslinker 5, hyperbranched polycarbonate with acrylate end groups | |
| 9.80 g | of methacrylic acid | |
| | Feed 3 | |
| 0.70 g | of a 75% strength by weight solution of tert-butyl perpivalate in aliphatic hydrocarbons | |
| 0.86 g | of dem. water | |
| | Feed 4 | |
| 5.38 g | of a 10% strength by weight aqueous solution of tert-butyl hydroperoxide | |
| | Feed 5 | |
| 28.30 g | of a 1.06% strength by weight aqueous solution of ascorbic acid | |

An emulsion was prepared and polymerized analogously to Example 1. This gave a dispersion with a solids content of 45.9% by weight, an average particle size of D[v, 0.5]=3.9 μm (number-average determined by means of light scattering) and an evaporation rate of 14.9%.

Example 5

The procedure was analogous to Example 4 except that the crosslinker used was hyperbranched polycarbonate with acrylate end groups (crosslinker 6).

This gave a dispersion with a solids content of 44.4% by weight, an average particle size of D[v, 0.5]=2.5 μm (number-average determined by means of light scattering) and an evaporation rate of 8.8%.

Example 6

The procedure was analogous to Example 4 except that 245.38 g of dem. water were used in the water phase and the crosslinker used was hyperbranched polyurethane with allyl end group (crosslinker 3).

This gave a dispersion with a solids content of 50% by weight, an average particle size of D[v, 0.5]=3.4 μm (number-average determined by means of light scattering) and an evaporation rate of 2.5%.

Example 7

| | Water phase | |
|---|---|---|
| 298.01 g | of dem. water (dem. = completely demineralized water) | |
| 195.60 g | of a 10% strength by weight aqueous solution of polyvinyl alcohol (Mowiol 18-88, Kuraray) | |
| 2.10 g | of a 2.5% strength by weight aqueous solution of sodium nitrite | |
| | Feed 1 | |
| 431.00 g | of octadecane | |
| 9.00 g | of paraffin with a melting point in the range from 65-75° C. | |
| | Feed 2 | |
| 19.60 g | of methyl methacrylate | |
| 19.60 g | of crosslinker 3 (hyperbranched polyurethane with allyl end groups) | |
| 9.80 g | of methacrylic acid | |
| | Feed 3 | |
| 0.70 g | of a 75% strength by weight solution of tert-butyl perpivalate in aliphatic hydrocarbons | |
| 0.86 g | of dem. water | |
| | Feed 4 | |
| 5.38 g | of a 10% strength by weight aqueous solution of ten-butyl hydroperoxide | |
| | Feed 5 | |
| 28.30 g | of a 1.06% strength by weight aqueous solution of ascorbic acid | |

An emulsion was prepared and polymerized analogously to Example 1. This gave a dispersion with a solids content of 49.6% by weight, an average particle size of D[v, 0.5]=6.0 μm (number-average determined by means of light scattering) and an evaporation rate of 3.9%.

Example 8

The procedure was as in Example 7 except that 128.02 g of dem. water were used in the water phase.

This gave a dispersion with a solids content of 60.6% by weight, an average particle size of D[v, 0.5]=2.6 μm (number-average determined by means of light scattering) and an evaporation rate of 2.6%.

Example 9

| | Water phase | |
|---|---|---|
| 127.91 g | of dem. water (dem. = completely demineralized water) | |
| 195.60 g | of a 10% strength by weight aqueous solution of polyvinyl alcohol (Mowiol 18-88, Kuraray) | |

| 2.20 g | of a 2.5% strength by weight aqueous solution of sodium nitrite |
|---|---|
| Feed 1 | |
| 431.00 g | of octadecane |
| 9.00 g | of paraffin with a melting point in the range from 65-75° C. |
| Feed 2 | |
| 19.60 g | of methyl methacrylate |
| 19.60 g | of hyperbranched polyurethane with acrylate end groups, crosslinker 2 |
| 9.80 g | of methacrylic acid |
| Feed 3 | |
| 0.70 g | of a 75% strength by weight solution of tert-butyl perpivalate in aliphatic hydrocarbons |
| 0.86 g | of dem. water |
| Feed 4 | |
| 5.38 g | of a 10% strength by weight aqueous solution of tert-butyl hydroperoxide |
| Feed 5 | |
| 28.31 g | of a 1.06% strength by weight aqueous solution of ascorbic acid |

An emulsion was prepared and polymerized analogously to Example 1.

This gave a dispersion with a solids content of 60.2% by weight, an average particle size of D[v, 0.5]=2.8 μm (number-average determined by means of light scattering) and an evaporation rate of 4.8%.

Example 10

Weighing, emulsification and polymerization were carried out analogously to Example 9 except that polyvinyl alcohol Mowiol 40-88 from Kuraray was used.

This gave a dispersion with a solids content of 59.8% by weight, an average particle size of D[v, 0.5]=2.8 μm (number-average determined by means of light scattering) and an evaporation rate of 4.9%.

Example 11

| Water phase | |
|---|---|
| 245.38 g | of dem. water (dem. = completely demineralized water) |
| 190.00 g | of a 5% strength by weight aqueous solution of methylhydroxypropylcellulose (Culmina) MHPC 100, Hercules Doel) |
| 47.50 g | of a 10% strength by weight aqueous solution of polyvinyl alcohol (Mowiol 15-79, Kuraray) |
| 2.20 g | of a 2.5% strength by weight aqueous solution of sodium nitrite |
| Feed 1 | |
| 431.00 g | of octadecane |
| 9.00 g | of paraffin with a melting point in the range from 65-75° C. |
| Feed 2 | |
| 19.60 g | of methyl methacrylate |
| 19.60 g | of crosslinker 1 (hyperbranched polyurethane with acrylate end groups) |
| 9.80 g | of methacrylic acid |
| Feed 3 | |
| 0.70 g | of a 75% strength by weight solution of tert-butyl perpivalate in aliphatic hydrocarbons |
| 0.86 g | of dem. water |
| Feed 4 | |
| 5.38 g | of a 10% strength by weight aqueous solution of tert-butyl hydroperoxide |
| Feed 5 | |
| 28.30 g | of a 1.06% strength by weight aqueous solution of ascorbic acid |

An emulsion was prepared and polymerized analogously to Example 1.

This gave a dispersion with a solids content of 49.3% by weight, an average particle size of D[v, 0.5]=5.6 μm (number-average determined by means of light scattering) and an evaporation rate of 6.7%.

Example 12

Weighing, emulsification and polymerization were carried out analogously to Example 11 except that 153.64 g of dem. water was used in the water phase.

This gave a dispersion with a solids content of 55.2% by weight, an average particle size of D[v, 0.5]=3.7 μm (number-average determined by means of light scattering) and an evaporation rate of 1.5%.

Example 13

Weighing, emulsification and polymerization were carried out analogously to Example 7 except that 434.00 g of dem. water were used in the water phase, as was crosslinker 1.

This gave a dispersion with a solids content of 44.0% by weight, an average particle size of D[v, 0.5]=8.3 μm (number-average determined by means of light scattering) and an evaporation rate of 10.2%.

Example 14

Weighing, emulsification and polymerization were carried out analogously to Example 7 except that the crosslinker used was a hyperbranched polyurethane with acrylate end groups (crosslinker 1).

This gave a dispersion with a solids content of 49.4% by weight, an average particle size of D[v, 0.5]=6.8 μm (number-average determined by means of light scattering) and an evaporation rate of 17.6%.

Example 15

Weighing, emulsification and polymerization were carried out analogously to Example 7 except that 205.29 g of dem. water were used in the water phase and the crosslinker used was a hyperbranched polyurethane with acrylate end groups (crosslinker 1).

This gave a dispersion with a solids content of 54.9% by weight, an average particle size of D[v, 0.5]=5.2 μm (number-average determined by means of light scattering) and an evaporation rate of 3.3%.

Example 16

Weighing, emulsification and polymerization were carried out analogously to Example 11 except that crosslinker 4 was used.

This gave a dispersion with a solids content of 49.6% by weight, an average particle size of $(D_{50})$=5.2 μm (number-average determined by means of light scattering) and an evaporation rate of 1.0%.

Example 17

Weighing, emulsification and polymerization were carried out analogously to Example 7 except that 434.00 g of dem. water were used in the water phase and that crosslinker 4 was used.

This gave a dispersion with a solids content of 43.8% by weight, an average particle size of D[v, 0.5]=7.6 µm (number-average determined by means of light scattering) and an evaporation rate of 1.3%.

Example 18

Weighing, emulsification and polymerization were carried out analogously to Example 7 except that 298.01 g of dem. water were used in the water phase and that crosslinker 4 was used.

This gave a dispersion with a solids content of 50.0% by weight, an average particle size of D[v, 0.5]=4.3 µm (number-average determined by means of light scattering) and an evaporation rate of 1.6%.

Example 19

Weighing, emulsification and polymerization were carried out analogously to Example 7 except that 146.02 g of dem. water were used in the water phase and that crosslinker 4 was used.

This gave a dispersion with a solids content of 59.9% by weight, an average particle size of D[v, 0.5]=3.2 µm (number-average determined by means of light scattering) and an evaporation rate of 1.3%.

The viscosity measurements in Examples 1 and 2 (not according to the invention) show that the viscosity usually increases at higher rotational speeds. By contrast, the microcapsule dispersions according to the invention show an at least constant viscosity. Especially at high solids contents, they even have a decreasing viscosity, which allows them to be advantageously processed.

The invention claimed is:
1. A microcapsule, comprising:
   a capsule core and
   a capsule wall,
   wherein the capsule wall is obtained by a process comprising polymerizing, in a free-radical polymerization, an oil-in-water emulsion,
   wherein the oil-in-water emulsion comprises the following monomers:
   (I) 30 to 90% by weight based on the total weight of the monomers of at least one monomer (I) selected from the group consisting of a $C_1$-$C_{24}$-alkyl ester of acrylic acid or of methacrylic acid or of both, acrylic acid, methacrylic acid, maleic acid, fumaric acid, and itaconic acid,
   (II) 10 to 70% by weight based on the total weight of the monomers of a monomer (II), which is an ethylenically unsaturated crosslinker, wherein at least 10% by weight, based on the total weight of the monomers (I), (II) and (III), is a highly branched polymeric crosslinker, and
   (III) 0 to 30% by weight based on the total weight of the monomers of a monomer (III), which is a monounsaturated monomer, which is different from monomer (I); and
   a hydrophobic core material.

TABLE 1

Results of the rheology measurements

| Example No. | SC [%] | Protective colloid | Crosslinker | Viscosity [mPa*s] 100 rpm | 250 rpm | 500 rpm |
| --- | --- | --- | --- | --- | --- | --- |
| 1 | 43.4 | methylhydroxypropylcellulose/polyvinyl alcohol | 1,4-butanediol diacrylate | 141 | 173 | 187 |
| 2 | 55.3 | polyvinyl alcohol | 1,4-butanediol diacrylate | 4100 | 6830 | 6410 |
| 3 | — | polyvinyl alcohol | 1,4-butanediol diacrylate | — | — | — |
| 4 | 45.9 | methylhydroxypropylcellulose/polyvinyl alcohol | crosslinker 5 | | | |
| 5 | 44.4 | methylhydroxypropylcellulose/polyvinyl alcohol | crosslinker 6 | | | |
| 6 | 50 | methylhydroxypropylcellulose/polyvinyl alcohol | crosslinker 3 | 329 | 443 | 549 |
| 7 | 49.6 | polyvinyl alcohol | crosslinker 3 | 609 | 604 | 577 |
| 8 | 60.6 | polyvinyl alcohol | crosslinker 3 | 14 800 | 10 800 | 8040 |
| 9 | 60.2 | polyvinyl alcohol | crosslinker 2 | 19 700 | 9220 | 5690 |
| 10 | 59.8 | polyvinyl alcohol (Mowiol 40-88) | crosslinker 2 | 12 400 | 5810 | 2330 |
| 11 | 49.3 | methylhydroxypropylcellulose/polyvinyl alcohol | crosslinker 1 | 1540 | 1950 | 1460 |
| 12 | 55.2 | methylhydroxypropylcellulose/polyvinyl alcohol | crosslinker 1 | 13 000 | 3290 | 2000 |
| 13 | 44.0 | polyvinyl alcohol | crosslinker 1 | 242 | 268 | 253 |
| 14 | 49.4 | polyvinyl alcohol | crosslinker 1 | 1210 | 1330 | 1280 |
| 15 | 54.9 | polyvinyl alcohol | crosslinker 1 | 11 700 | 6560 | 1830 |
| 16 | 49.6 | methylhydroxypropylcellulose/polyvinyl alcohol | crosslinker 4 | 486 | 787 | 934 |
| 17 | 43.8 | polyvinyl alcohol | crosslinker 4 | 204 | 229 | 210 |
| 18 | 50.0 | polyvinyl alcohol | crosslinker 4 | 484 | 499 | 490 |
| 19 | 59.9 | polyvinyl alcohol | crosslinker 4 | 15 200 | 10 500 | 724 |

SC: solids content

2. The microcapsule of claim 1, wherein the highly branched polymeric crosslinker is a hyperbranched polymer with a double bond content of from 0.1 to 10 mol/kg.

3. The microcapsule of claim 1, wherein the highly branched polymeric crosslinker is a polyaddition product or polycondensation product.

4. The microcapsule of claim 1, wherein the highly branched crosslinker is selected from the group consisting of a polycarbonate, a polyester, a polyether, a polyurethane, a polyurea, a polyamide, and mixtures thereof.

5. The microcapsule of claim 1, wherein the highly branched crosslinker is a polyester, a polycarbonate, a polyurethane, or a mixture thereof.

6. The microcapsule of claim 1, wherein
a total content of all monomer (I) is from 40 to 70% by weight based on the total weight of the monomers,
a total content of all monomer (II) is from 30% to 60% by weight based on the total weight of the monomers, wherein a total content of the highly branched polymeric crosslinker is at least 30% by weight based on the total weight of the monomers (I), (II) and (III), and
a total content of all monomer (III) is from 0 to 30%.

7. The microcapsule of claim 1, wherein the free-radical polymerization is in the presence a protective colloid.

8. The microcapsule of claim 7, wherein the protective colloid comprises a polyvinyl alcohol, a partially hydrolyzed polyvinyl acetate, a methylhydroxy($C_1$-$C_4$)-alkylcellulose, or a mixture thereof.

9. The microcapsule of claim 1, wherein the hydrophobic core material is at least one material selected from the group consisting of an aliphatic or aromatic hydrocarbon compound; a saturated or unsaturated $C_6$-$C_{30}$-fatty acid; a fatty alcohol; a $C_6$-$C_{30}$-fatty amine; a $C_4$-$C_{30}$-mono-, $C_4$-$C_{30}$-di-, or $C_4$-$C_{30}$-polyester; a primary, secondary or tertiary $C_4$-$C_{30}$-carboxamide; a fatty acid ester; a natural or synthetic wax; a halogenated hydrocarbon; a natural oil; a $C_3$-$C_{20}$-ketone; a $C_3$-$C_{20}$-aldehyde; a crosslinker; an adhesive resin; a tackifying resin; a fragrance; an aroma substance; an active compound; a dye; a color former; a catalyst; and an inhibitor.

10. A process for preparing a microcapsule, the process comprising:
forming a microcapsule which comprises capsule core and a capsule wall, wherein said forming comprises polymerizing, in a the free-radical polymerization, an oil-in-water emulsion,
wherein the oil-in-water emulsion comprises the following monomers:
(I) 30 to 90% by weight based on the total weight of the monomers of at least one monomer (I) selected from the group consisting of a $C_1$-$C_{24}$-alkyl ester of acrylic acid or of methacrylic acid or of both; acrylic acid; methacrylic acid; maleic acid; fumaric acid; and itaconic acid,
(II) 10 to 70% by weight based on the total weight of the monomers of a monomer (II), which is an ethylenically unsaturated crosslinker, wherein at least 10% by weight, based on the total weight of the monomers (I), (II) and (III), is a highly branched polymeric crosslinker, and
(III) 0 to 30% by weight based on the total weight of the monomers of a monomer (III), which is a monounsaturated monomer, which is different from monomer (I); and
a hydrophobic core material.

11. A latent heat storage material, comprising the microcapsule of claim 1.

12. The microcapsule of claim 4, wherein the highly branched crosslinker is at least one crosslinker selected from the group consisting of a poly(urea urethane), a poly(ether amine), a poly(ester amine), a poly(ether amide), a poly(ester amide), a poly(amidoamine), a poly(ester carbonate), a poly(ether carbonate), a poly(ether ester), and a poly(ether ester carbonate).

13. The process of claim 10, wherein the oil-in-water emulsion further comprises a protective colloid.

14. The microcapsule of claim 1, wherein the highly branched polymeric crosslinker has a molar mass distribution such that the width of the molar mass distribution is at least 1.1.

15. The microcapsule of claim 1, wherein the highly branched polymeric crosslinker has a degree of branching per molecule of from 10 to 100%.

16. The microcapsule of claim 1, wherein the highly branched polymeric crosslinker has at least 2 to 100, on number-average, ethylenically unsaturated end groups and/or side groups.

17. The microcapsule of claim 1, wherein the highly branched polymeric crosslinker has a weight-average molecular weight Mw of from about 800 to 300 000.

18. The process of claim 10, wherein the highly branched polymeric crosslinker has a molar mass distribution such that the width of the molar mass distribution is at least 1.1.

19. The process of claim 10, wherein the highly branched polymeric crosslinker has a degree of branching per molecule of from 10 to 100%.

20. The process of claim 10, wherein the highly branched polymeric crosslinker has at least 2 to 100, on number-average, ethylenically unsaturated end groups and/or side groups.

21. The process of claim 10, wherein the highly branched polymeric crosslinker has a weight-average molecular weight Mw of from about 800 to 300 000.

* * * * *

UNITED STATES PATENT AND TRADEMARK OFFICE
CERTIFICATE OF CORRECTION

PATENT NO. : 9,056,302 B2
APPLICATION NO. : 13/376226
DATED : June 16, 2015
INVENTOR(S) : Marc Rudolf Jung et al.

Page 1 of 1

It is certified that error appears in the above-identified patent and that said Letters Patent is hereby corrected as shown below:

On the title page, Item (75), the 2nd Inventor's information is incorrect.
Item (75) should read:

-- (75) Inventors:     Marc Rudolf Jung, Worms (DE);
                        Francisco Javier Lopez Villanueva, Mannheim (DE);
                        Tina Schroeder-Grimonpont, Rheinzabern (DE);
                        Monika Haberecht, Ludwigshafen (DE);
                        Bernd Bruchmann, Freinsheim (DE) --

Signed and Sealed this
Twentieth Day of October, 2015

Michelle K. Lee
*Director of the United States Patent and Trademark Office*